(12) United States Patent
MacDonald et al.

(10) Patent No.: US 6,201,104 B1
(45) Date of Patent: Mar. 13, 2001

(54) ANGIOGENESIS—INHIBITING PROTEIN BINDING PEPTIDES AND PROTEINS AND METHODS OF USE

(75) Inventors: Nicholas J. MacDonald, Chevy Chase; Kim Lee Sim, Gaithersburg, both of MD (US)

(73) Assignee: EntreMed, Inc., Rockville, MD (US)

( * ) Notice: Subject to any disclaimer, the term of this patent is extended or adjusted under 35 U.S.C. 154(b) by 0 days.

(21) Appl. No.: 09/206,059

(22) Filed: Dec. 4, 1998

(51) Int. Cl.[7] .................................................. C07K 14/705
(52) U.S. Cl. .......................... 530/327; 530/350; 435/69.1
(58) Field of Search .................................. 530/327, 350; 435/69.1

(56) References Cited

U.S. PATENT DOCUMENTS

| | | | |
|---|---|---|---|
| 5,639,725 | 6/1997 | O'Reilly et al. | 514/12 |
| 5,733,876 | 3/1998 | O'Reilly et al. | 514/12 |
| 5,854,205 | * 12/1998 | O'Reilly et al. | 514/2 |

FOREIGN PATENT DOCUMENTS

| | | |
|---|---|---|
| WO 95/29242 | 11/1995 | (WO) . |
| WO 97/15666 | 5/1997 | (WO) . |

OTHER PUBLICATIONS

Chen, C. et al., "A Strategy to Discover Circulating Angiogenesis Inhibitors Generated by Human Tumors", *Canc. Res.*, vol. 55, pp. 4230–4233 (1995).

Folkman, J., "What is the Evidence that Tumors are Angiogenesis Dependent?", *J. Natl. Canc. Inst.*, vol. 82, pp. 4–6 (1990).

Folkman, J. et al., "Induction of angiogenesis during the transition from hyperplasia to neoplasia", *Nature*, vol. 339, pp. 58–61 (1989).

Folkman, J., "Angiogenesis and Its Inhibitors", *Important Advances in Oncology*, J.B. Lippincott Company, pp. 42–62 (1985).

Grant, D.S. et al., "Two different laminin domains mediate the differentiation of human endothelial cells into capillary–like structures in vitro", *Cell*, vol. 58, pp. 933–943 (1989).

Kivirikko, S. et al., "Primary Structure of the α1 Chain of Human Type XV Collagen and Exon–Intron Organization in the 3'Region of the Corresponding Gene", *J. Biol. Chem.*, vol. 269, No. 7, pp. 4773–4779 (1994).

Nelson, J. et al., "Murine epidermal growth factor (EGF) fragment (33–42) inhibits both EGF–and laminin–dependent endothelial cell motility and angiogenesis", *Canc. Res.*, vol. 55, pp. 3772–3776 (1995).

O'Reilly et al., "Endogenous Inhibitors of Angiogenesis", *Proc. Am. Assoc. Canc. Res.*, vol. 37, p. 669 (1996) (Abstract only).

O'Reilly et al., "The suppression of Tumor Metastases by a Primary Tumor", *Surgical Forum*, vol. XLIV, pp. 474–476 (1993).

O'Reilly et al., "Angiostatin: A Novel Angiogenesis Inhibitor that Mediates the Suppression of Metastases by a Lewis Lung Carcinoma", *Cell*, vol. 79, pp. 315–328 (1994).

O'Reilly et al., "Angiostatin: A Circulating Endothelial Cell Inhibitor That Suppresses Angiogenesis and Tumor Growth", *Cold Spring Harbor Symposia on Quantitative Biology*, vol. LIX, pp. 471–482 (1994).

Rehn, M. et al., "α1(XVIII), a collagen chain with frequent interruptions in the collagenous sequence, a distinct tissue distribution, and homology with type XV collagen", *Proc. Natl. Acad. Sci. USA*, vol. 91, pp. 4234–4238 (1994).

Rehn, M. et al., "Identification of three N–terminal ends of type XVIII collagen chains and tissue–specific differences in the expression of the corresponding transcripts", *J. Biol. Chem.*, vol. 270, pp. 4705–4711 (1995).

Robbins, K.C., "The Plasminogen–Plasmin Enzyme System", *Fibrinolysis*, pp. 340–357 (1987).

Folkman, Judah, "Tumor Angiogenesis: Therapeutic Implications", *The New England Journal of Medicine*, vol. 285, No. 21, Nov. 18, 1971, pp. 1182–1186.

* cited by examiner

*Primary Examiner*—Prema Mertz
(74) *Attorney, Agent, or Firm*—Kilpatrick Stockton LLP

(57) ABSTRACT

The present invention relates to peptides and proteins such as receptors that bind angiogenesis-related proteins ANGIOSTATIN™ protein or ENDOSTATIN™ protein. Peptides and proteins of the present invention can be isolated from body fluids including blood or urine, or can be synthesized by recombinant, enzymatic or chemical methods. The peptides are particularly important for identifying receptors of angiogenesis-related proteins, as well as for identifying other proteins that regulate, transport and otherwise interact with angiogenesis-related proteins.

6 Claims, 7 Drawing Sheets

FIGURE 2

Leu Phe Glu Lys Lys Val Tyr Leu Ser Glu Cys Lys Thr Gly Asn Gly Lys
Asn Tyr Arg Gly Thr Met Ser Lys Thr Lys Asn Gly Ile Thr Cys Gln Lys
Trp Ser Ser Thr Ser Pro His Arg Pro Arg Phe Ser Pro Ala Thr His Pro
Ser Glu Gly Leu Glu Glu Asn Tyr Cys Arg Asn Pro Asp Asn Asp Pro
Gln Gly Pro Trp Cys Tyr Thr Thr Asp Pro Glu Lys Arg Tyr Asp Tyr Cys
Asp Ile Leu Glu Cys Glu Glu Glu Cys Met His Cys Ser Gly Glu Asn Tyr
Asp Gly Lys Ile Ser Lys Thr Met Ser Gly Leu Glu Cys Gln Ala Trp Asp
Ser Gln Ser Pro His Ala His Gly Tyr Ile Pro Ser Lys Phe Pro Asn Lys
Asn Leu Lys Lys Asn Tyr Cys Arg Asn Pro Asp Arg Glu Leu Arg Pro
Trp Cys Phe Thr Thr Asp Pro Asn Lys Arg Trp Glu Leu Cys Asp Ile Pro
Arg Cys Thr Thr Pro Pro Pro Ser Ser Gly Pro Thr Tyr Gln Cys Leu Lys
Gly Thr Gly Glu Asn Tyr Arg Gly Asn Val Ala Val Thr Val Ser Gly His
Thr Cys Gln His Trp Ser Ala Gln Thr Pro His Thr His Asn Arg Thr Pro
Glu Asn Phe Pro Cys Lys Asn Leu Asp Glu Asn Tyr Cys Arg Asn Pro
Asp Gly Lys Arg Ala Pro Trp Cys His Thr Thr Asn Ser Gln Val Arg Trp
Glu Tyr Cys Lys Ile Pro Ser Cys Asp Ser Ser Pro Val Ser Thr Glu Gln
Leu Ala Pro Thr Ala Pro Pro Glu Leu Thr Pro Val Val Gln Asp Cys Tyr
His Gly Asp Gly Gln Ser Tyr Arg Gly Thr Ser Ser Thr Thr Thr Thr Gly
Lys Lys Cys Gln Ser Trp Ser Ser Met Thr Pro His Arg His Gln Lys Thr
Pro Glu Asn Tyr Pro Asn Ala Gly Leu Thr Met Asn Tyr Cys Arg Asn
Pro Asp Ala Asp Lys Gly Pro Trp Cys Phe Thr Thr Asp Pro Ser Val Arg
Trp Glu Tyr Cys Asn Leu Lys Lys Cys Ser Gly Thr Glu Ala Ser Val Val
Ala Pro Pro Pro Val Val Leu Leu

FIGURE 3

His Ser His Arg Asp Phe Gln Pro Val Leu His Leu Val Ala Leu Asn Ser
Pro Leu Ser Gly Gly Met Arg Gly Ile Arg Gly Ala Asp Phe Gln Cys Phe
Gln Gln Ala Arg Ala Val Gly Leu Ala Gly Thr Phe Arg Ala Phe Leu Ser
Ser Arg Leu Gln Asp Leu Tyr Ser Ile Val Arg Arg Ala Asp Arg Ala Ala
Val Pro Ile Val Asn Leu Lys Asp Glu Leu Leu Phe Pro Ser Trp Glu Ala
Leu Phe Ser Gly Ser Glu Gly Pro Leu Lys Pro Gly Ala Arg Ile Phe Ser
Phe Asp Gly Lys Asp Val Leu Arg His Pro Thr Trp Pro Gln Lys Ser Val
Trp His Gly Ser Asp Pro Asn Gly Arg Arg Leu Thr Glu Ser Tyr Cys Glu
Thr Trp Arg Thr Glu Ala Pro Ser Ala Thr Gly Gln Ala Ser Ser Leu Leu
Gly Gly Arg Leu Leu Gly Gln Ser Ala Ala Ser Cys His His Ala Tyr Ile
Val Leu Cys Ile Glu Asn Ser Phe Met Thr Ala Ser Lys

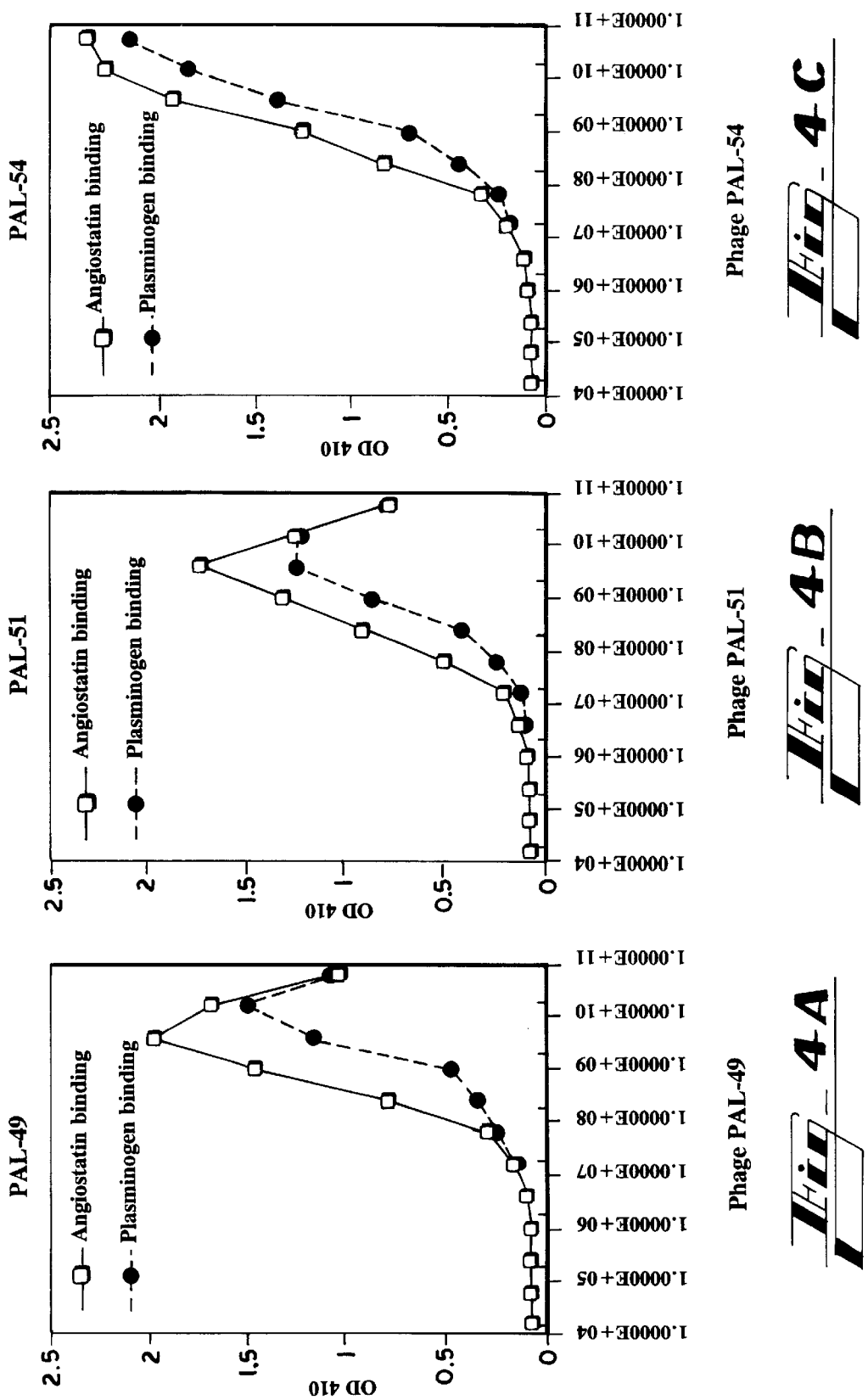

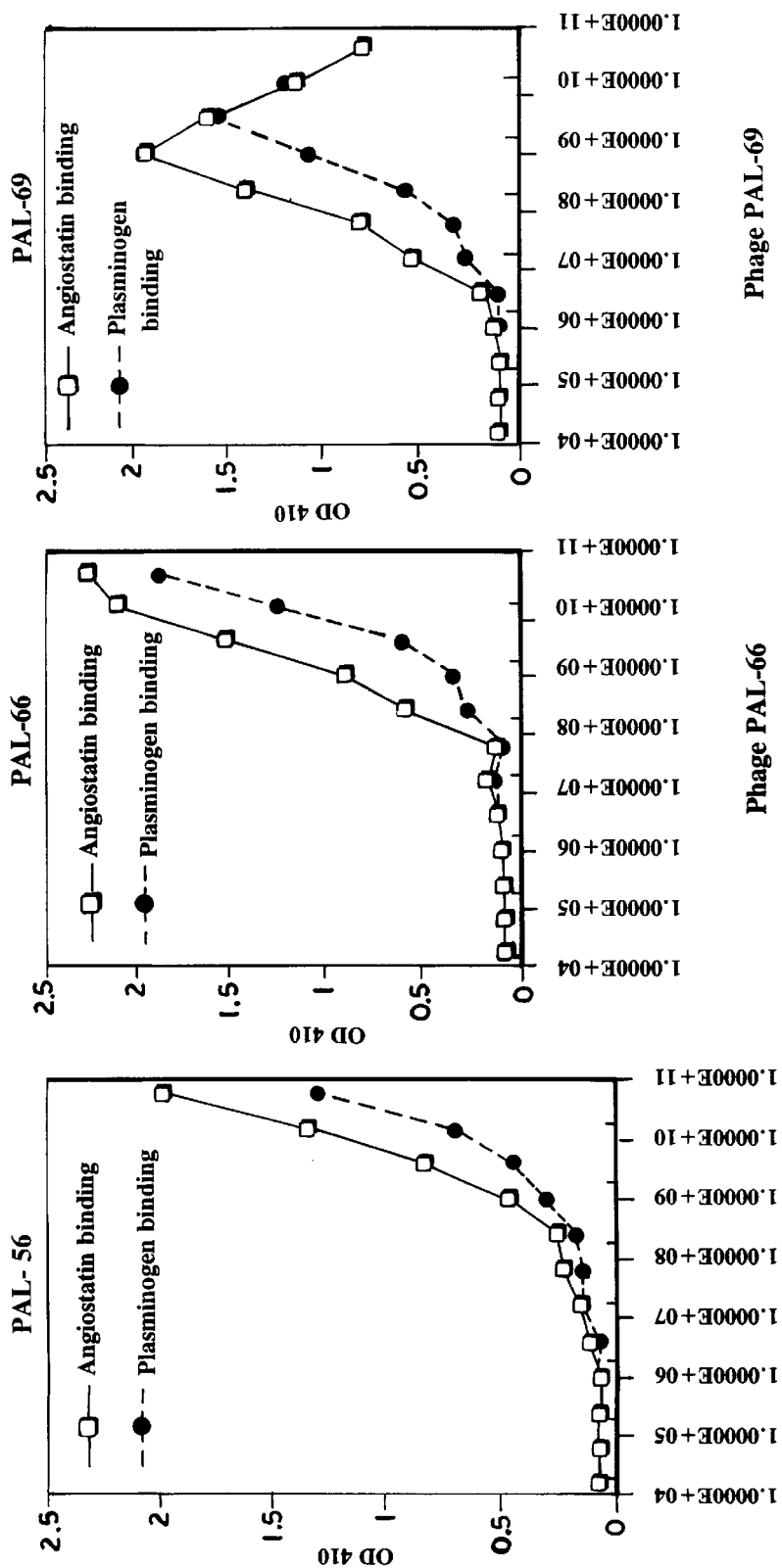

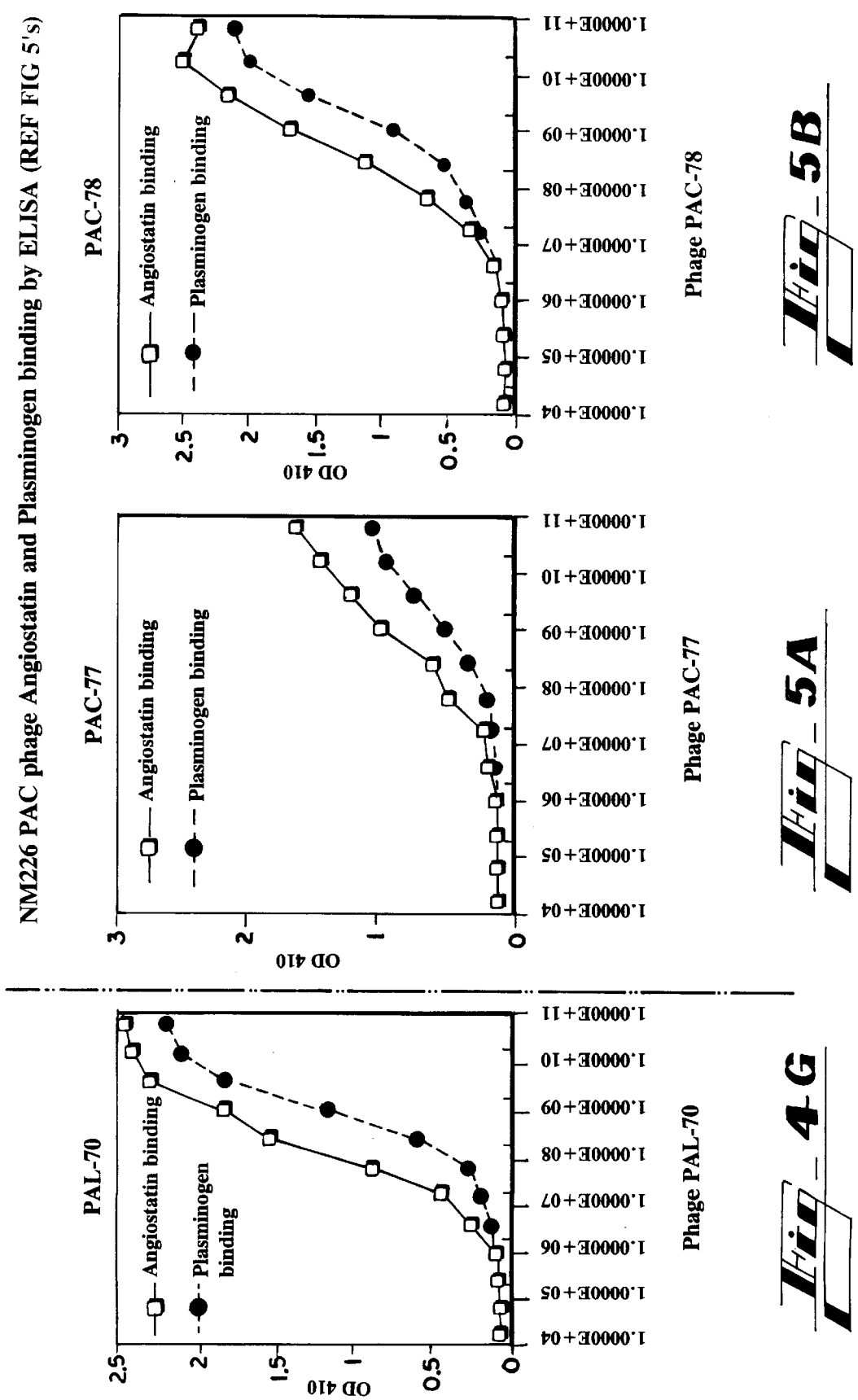

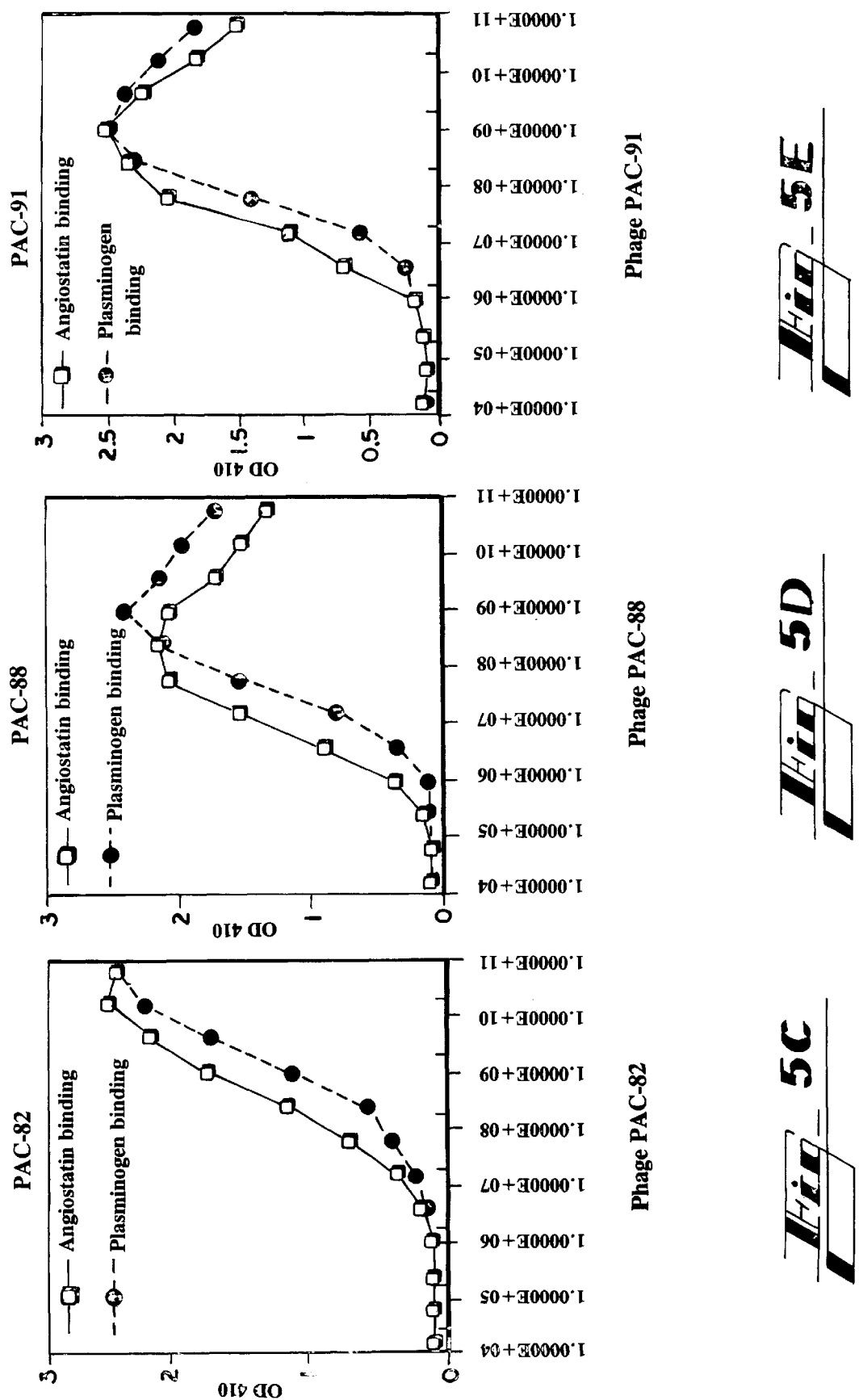

ANGIOGENESIS— INHIBITING PROTEIN BINDING PEPTIDES AND PROTEINS AND METHODS OF USE

FIELD OF THE INVENTION

The present invention relates to peptides and proteins that bind angiogenesis-related proteins, such as ANGIOSTATIN™ protein or ENDOSTATIN™ protein. Peptides and proteins of the present invention can be isolated from body fluids and tissues including blood or urine, or can be synthesized by recombinant, enzymatic or chemical methods. In addition, the present invention relates to the use of such binding molecules in diagnostic assays and kits for protein measurement, histochemical kits for protein localization, nucleotide sequences coding for protein, and molecular probes for monitoring protein biosynthesis, wherein the protein is related to angiogenesis.

BACKGROUND OF THE INVENTION

As used herein, the term "angiogenesis" means the generation of new blood vessels into a tissue or organ. Under normal physiological conditions, humans or animals undergo angiogenesis only in very specific restricted situations. For example, angiogenesis is normally observed in wound healing, fetal and embryonal development and formation of the corpus luteum, endometrium and placenta. The term "endothelium" means a thin layer of flat epithelial cells that lines serous cavities, lymph vessels, and blood vessels.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane.

Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops thereby creating the new blood vessel.

Persistent, unregulated angiogenesis occurs in a multiplicity of disease states, tumor metastasis and abnormal growth by endothelial cells and supports the pathological damage seen in these conditions. The diverse pathological disease states in which unregulated angiogenesis is present have been grouped together as angiogenic-dependent or angiogenic-associated diseases.

The hypothesis that tumor growth is angiogenesis-dependent was first proposed in 1971. (Folkman J., Tumor angiogenesis: Therapeutic implications., N. Engl. Jour. Med. 285:1182 1186, 1971) In its simplest terms it states: "Once tumor 'take' has occurred, every increase in tumor cell population must be preceded by an increase in new capillaries converging on the tumor." Tumor "take" is currently understood to indicate a prevascular phase of tumor growth in which a population of tumor cells occupying a few cubic millimeters volume and not exceeding a few million cells, can survive on existing host microvessels. Expansion of tumor volume beyond this phase requires the induction of new capillary blood vessels. For example, pulmonary micrometastases in the early prevascular phase in mice would be undetectable except by high power microscopy on histological sections.

It is clear that angiogenesis plays a major role in the metastasis of a cancer. If this angiogenic activity could be repressed or eliminated, then the tumor, although present, would not grow. In the disease state, prevention of angiogenesis could avert the damage caused by the invasion of the new microvascular system. Therapies directed at control of the angiogenic processes could lead to the abrogation or mitigation of these diseases.

One example of a disease mediated by angiogenesis is ocular neovascular disease. This disease is characterized by invasion of new blood vessels into the structures of the eye such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia. Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegener's sarcoidosis, Scleritis, Steven's Johnson disease, periphigoid radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales disease, Bechet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, trauma and post-laser complications. Other diseases include, but are not limited to, diseases associated with rubeosis (neovascularization of the angle) and diseases caused by the abnormal proliferation of fibrovascular or fibrous tissue including all forms of proliferative vitreoretinopathy.

Another disease in which angiogenesis is believed to be involved is rheumatoid arthritis. The blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Factors associated with angiogenesis may also have a role in osteoarthritis. The activation of the chondrocytes by angiogenic-related factors contributes to the destruction of the joint. At a later stage, the angiogenic factors would promote new bone formation. Therapeutic intervention that prevents the bone destruction could halt the progress of the disease and provide relief for persons suffering with arthritis.

Chronic inflammation may also involve pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Numerous efforts have been made by researchers in the pharmaceutical industry to improve the target specificity of drugs. As is familiar to those skilled in the art, the manifestation of a disease many times involves the display of a particular cell type or protein as an antigenic, epitopic, or surface marker. In such instances, an antibody can be raised against the unique cell surface marker and a drug can be linked to the antibody. Upon administration of the drug/antibody complex to a patient, the binding of the antibody to the cell surface marker results in the delivery of a relatively high concentration of the drug to the diseased tissue or organ. Similar methods can be used where a particular cell type in the diseased organ expresses a unique cell surface receptor or a ligand for a particular receptor. In these cases, the drug can be linked to the specific ligand or to the receptor, respectively, thus providing a means to deliver a relatively high concentration of the drug to the diseased organ.

One of the important proteins involved in angiogenesis is ANGIOSTATIN™ protein. (see U.S. Pat. No. 5,639,725 to O'Reilly et al., which is incorporated in its entirety by reference herein). ANGIOSTATIN™ protein preferably has a molecular weight of between approximately 38,000 Daltons and 45,000 Daltons as determined by reducing polyacrylamide gel electrophoresis, and has an amino acid sequence substantially similar to that of a plasminogen fragment beginning at approximately amino acid number 98 of an intact plasminogen molecule. ANGIOSTATIN™ protein has "endothelial inhibiting activity" such that it has the capability to inhibit angiogenesis in general and, for example, to inhibit the growth of bovine capillary endothelial cells in culture in the presence of fibroblast growth factor.

ANGIOSTATIN™ protein may be produced from recombinant sources, from genetically altered cells implanted into animals, from tumors, and from cell cultures as well as other sources. ANGIOSTATIN™ protein can be isolated from body fluids including, but not limited to, serum and urine. Recombinant techniques include gene amplification from DNA sources using the polymerase chain reaction (PCR), and gene amplification from RNA sources using reverse transcriptase/PCR.

ANGIOSTATIN™ protein has been shown to be capable of inhibiting the growth of endothelial cells in vitro and in vivo. ANGIOSTATIN™ protein does not inhibit the growth of cell lines derived from other cell types. Specifically, ANGIOSTATIN™ protein has no effect on Lewis lung carcinoma cell lines, mink lung epithelium, 3T3 fibroblasts, bovine aortic smooth muscle cells, bovine retinal pigment epithelium, MDCk cells (canine renal epithelium), WI38 cells (human fetal lung fibroblasts), EFN cells (murine fetal fibroblasts) and LM cells (murine connective tissue). Endogenous ANGIOSTATIN™ protein in a tumor bearing mouse is effective at inhibiting metastases at a systemic concentration of approximately 10 mg ANGIOSTATIN™ protein/kg body weight.

ANGIOSTATIN™ protein has a specific three dimensional conformation that is defined by the kringle region of the plasminogen molecule. (Robbins, K. C., "The plasminogen-plasmin enzyme system" Hemostasis and Thrombosis, Basic Principles and Practice, 2nd Edition, ed. by Colman, R. W. et al. J.B. Lippincott Company, pp. 340–357, 1987). There are five such kringle regions, which are conformationally related motifs and have substantial sequence homology in the amino terminal portion of the plasminogen molecule. See FIG. 1 for a schematic diagram of the structure of the plasminogen molecule.

The amino acid sequence of the complete murine plasminogen molecule is shown in SEQ ID NO:81.

A preferred amino acid sequence for human ANGIOSTATIN™ protein as shown in FIG. 2.

As used herein, "kringle 1" means a protein derivative of plasminogen having an endothelial cell inhibiting activity, and having an amino acid sequence comprising a sequence homologous to kringle 1, exemplified by, but not limited to that of human kringle 1 corresponding to amino acid positions 11 to 90 (inclusive) of ANGIOSTATIN™ protein of SEQ ID NO: 1. As used herein, "kringle 2" is exemplified by, but not limited, to amino acid positions 94 to 172 (inclusive) of ANGIOSTATIN™ protein of SEQ ID NO:1. As used herein, "kringle 3" is exemplified by, but not limited to, amino acid positions 185 to 263 (inclusive) of ANGIOSTATIN™ protein of SEQ ID NO:1. As used herein, "kringle 4" is exemplified by, but not limited to, amino acid positions 288 to 366 (inclusive) of ANGIOSTATIN™ protein of SEQ ID NO:1.

Furthermore, it is understood that a variety of silent amino acid substitutions, additions, or deletions can be made in the above identified kringle fragments, which do not significantly alter the fragments' endothelial cell inhibiting activity, and which are, therefore, not intended to exceed the scope of the claims.

Each kringle region of the plasminogen molecule contains approximately 80 amino acids and contains 3 disulfide bonds. Anti-angiogenic ANGIOSTATIN™ protein may contain a varying amount of amino- or carboxy-terminal amino acids from the interkringle regions and may have some or all of the naturally occurring di-sulfide bonds reduced. ANGIOSTATIN™ protein may also be provided in an aggregate, non-refolded, recombinant form. Additionally, individual and groups of kringle peptides may be useful for inhibition of angiogenesis (see PCT/US96/05856, which is incorporated herein by reference).

The cDNA sequence for human ANGIOSTATIN™ protein is provided as SEQ ID NO:29.

It is contemplated that any isolated protein or peptide having a three dimensional kringle-like conformation or cysteine motif that has anti-angiogenic activity in vivo, is also an ANGIOSTATIN™ protein compound. The amino acid sequence of the ANGIOSTATIN™ protein of the present invention may vary depending upon, for example, from which species the plasminogen molecule is derived. Thus, although the ANGIOSTATIN™ protein of the present invention that is derived from human plasminogen has a slightly different sequence than ANGIOSTATIN™ protein derived from mouse, it has anti-angiogenic activity as shown in a mouse tumor model.

Another important angiogenesis-related protein is ENDOSTATIN™ protein. (see U.S. Pat. No. 5,854,25 and WO 97/15666 O'Reilly et al., both of which are incorporated in their entirety by reference herein) ENDOSTATIN™ protein is a potent and specific inhibitor of endothelial proliferation and angiogenesis. Systemic therapy with ENDOSTATIN™ protein causes a nearly complete suppression of tumor induced angiogenesis.

ENDOSTATIN™ protein has a molecular weight of approximately 18,000 to approximately 20,000 Daltons as determined by non-reduced and reduced gel electrophoresis, respectively, and is capable of inhibiting endothelial cell proliferation in cultured endothelial cells. ENDOSTATIN™ protein has an amino acid sequence substantially similar to a fragment of a collagen molecule and whereas it binds to a heparin affinity column, it does not bind to a lysine affinity column.

ENDOSTATIN™ protein can be isolated from murine hemangioendothelioma EOMA. ENDOSTATIN™ protein may also be produced from recombinant sources, from genetically altered cells implanted into animals, from tumors, and from cell cultures as well as other sources. ENDOSTATIN™ protein can be isolated from body fluids including, but not limited to, serum and urine. Recombinant techniques include gene amplification from DNA sources using the polymerase chain reaction (PCR), and gene amplification from RNA sources using reverse transcriptase/PCR.

Alternatively, endothelial proliferation inhibiting proteins, or ENDOSTATIN™ proteins, of the present invention may be isolated from larger known proteins, such as human alpha 1 type XVIII collagen and mouse alpha 1 type XVIII collagen, proteins that share a common or similar N-terminal amino acid sequence. Examples of other potential ENDOSTATIN™ protein source materials having similar N-terminal amino acid sequences include Bos taurus pregastric esterase, human alpha 1 type XV collagen, NAD-dependent formate dehydrogenase (EC 1.2.1.2) derived from Pseudomonas sp., s11459 hexon protein of bovine adenovirus type 3, CELF21D12 2 F21d12.3 Caenorhabditis elegans gene product, VAL1 TGMV AL1 protein derived from tomato golden mosaic virus, s01730 hexon protein derived from human adenovirus 12, and *Saccharomyces cerevisiae.*

Human ENDOSTATIN™ can be further characterized by its preferred amino acid sequence as set forth in FIG. 3 and in SEQ ID NO: 2. The preferred sequence of the first 20 amino-terminal amino acids corresponds to a C-terminal fragment of collagen type XVIII or collagen type XV. Specifically, in one embodiment the amino terminal amino acid sequence of ENDOSTATIN™ protein corresponds to an internal 20 amino acid peptide region found in mouse collagen alpha 1 type XVIII starting at amino acid 1105 and ending at amino acid 1124. The amino terminal amino acid sequence of the inhibitor also corresponds to an internal 20 amino acid peptide region found in human collagen alpha 1 type XVIII starting at amino acid 1132 and ending at amino acid 1151. The cDNA sequence for ENDOSTATIN™ protein is provided as SEQ ID NO: 30.

Both ANGIOSTATIN™ protein and ENDOSTATIN™ protein specifically and reversibly inhibit endothelial cell proliferation and may be used, for example, as a birth control drug, for treating angiogenesis-related diseases, particularly angiogenesis-dependent cancers and tumors, and for curing angiogenesis-dependent cancers and tumors. Therapies directed at control of the angiogenic processes could lead to the abrogation or mitigation of such diseases mediated by angiogenesis. Potential therapies useful for controlling angiogenic processes may involve recognition of antigenic markers and receptors associated with angiogenesis and subsequent modification of such markers and receptors. For example, once a receptor for an angiogenesis-related protein is identified, it can be blocked, thereby inhibiting the effect of the angiogenesis-related protein and ultimately reducing angiogenesis.

One technique that is useful for identifying antigenic markers and receptors is phage-display technology. (see for example Phage Display of Peptides and Proteins: A Laboratory Manual. Edited by Brian K. Kay et al. Academic Press San Diego, 1996) Phage-display technology is a powerful tool for the identification of individual epitopes that interact with ligands such as proteins and antibodies. Phage peptide libraries typically comprise numerous different phage clones, each expressing a different peptide, encoded in a single-stranded DNA genome as an insert in one of the coat proteins. In an ideal phage library the number of individual clones would be $20^n$, where "n" equals the number of residues that make up the random peptides encoded by the phage. For example, if a phage library was screened for a seven residue peptide, the library in theory would contain $20^7$ (or $1.28 \times 10^9$) possible 7-residue sequences. Therefore, a 7-mer peptide library should contain approximately $10^9$ individual phage.

Phage clones displaying peptides that are able to mimic epitopes recognized by a particular protein (or antibody), are selected from the library based upon their binding affinity to that protein (or antibody), and the sequences of the inserted peptides are deduced from the DNA sequences of the phage clones. This approach is particularly desirable because no prior knowledge of the primary sequence of the target protein is necessary, epitopes represented within the target, either by a linear sequence of amino acids (linear epitope) or by the spatial juxtaposition of amino acids distant from each other within the primary sequence (conformational epitope) are both identifiable, and peptidic mimotopes of epitopes derived from nonproteinaceous molecules such as lipids and carbohydrate moieties can also be generated.

With regard to angiogenesis-related disease, it is evident that angiogenesis-related proteins such as ANGIOSATIN™ protein and ENDOSTATIN™ protein play an important role in the development of disorders such as cancer. What is needed therefore, is the development of methods and compositions for the identification of receptors and molecules that bind such proteins. The identification of such receptors and molecules would facilitate the understanding of angiogenesis-related protein influence and interaction, and consequently enable the development of drugs to modify the activity of these proteins as necessary.

SUMMARY OF THE INVENTION

In accordance with the present invention, compositions and methods are provided that are effective for modulating angiogenesis, and inhibiting all forms of unwanted angiogenesis, especially angiogenesis related to tumor growth. Specifically, the present invention includes peptides and proteins that bind to angiogenesis-related peptides and proteins, such as ANGIOSTATIN™ protein or ENDOSTATIN™ protein. Identification of these binding molecules and proteins has improved the understanding of angiogenesis-related protein influence, and has also made possible the development of therapeutic agents for modifying angiogenesis related to disorders such as cancer and tumor development.

ANGIOSTATIN™ protein and ENDOSTATIN™ protein are defined by their ability to inhibit the angiogenic activity of endogenous growth factors such as bFGF on endothelial cells, in vitro and tumor growth in vivo. ANGIOSTATIN™ protein contains approximately kringle regions 1 through 4 of plasminogen and is a protein having a molecular weight of between approximately 38,000 Daltons and 45,000 Daltons as determined by reducing polyacrylamide gel electrophoresis. In a preferred embodiment, ANGIOSTATIN™ protein has an amino acid sequence substantially similar to that of a fragment of murine plasminogen beginning at amino acid number 98.

ENDOSTATIN™ protein is a collagen fragment, and is a protein having a molecular weight of between approximately 18,000 Daltons and 20,000 Daltons as determined by non-reducing and reducing gel electrophoresis, respectively. ENDOSTATIN™ protein is further characterized by its ability to bind a heparin affinity column and inability to bind a lysine affinity column. A preferred sequence of the first 20 N-terminal amino acids of ENDOSTATIN™ protein corresponds to a C-terminal fragment of collagen type XVIII or XV.

The present invention also encompasses nucleotide sequences encoding peptides and proteins that bind angiogenesis-related peptides and proteins, as well as expression vectors containing nucleotide sequences encoding such binding peptides and proteins, and cells containing one or more expression vectors containing nucleotide sequences encoding such peptides and proteins. The present invention further encompasses gene therapy methods whereby nucleotide sequences encoding angiogenesis related protein binding peptides and proteins are introduced into a patient to modify in vivo ANGIOSTATIN™ protein or ENDOSTATIN™ protein levels.

The present invention also includes diagnostic methods and kits for detection and measurement of peptides and proteins that bind angiogenesis-related proteins in biological fluids and tissues, and for localization of such peptides and proteins in tissues and cells. The diagnostic method and kit can be in any configuration well known to those of ordinary skill in the art.

The present invention includes peptides and proteins that bind ANGIOSTATIN™ protein or ENDOSTATIN™ protein and cause the transmission of an appropriate signal to a cell and act as agonists or antagonists of angiogenesis.

In addition, the present invention includes fragments of proteins that bind angiogenesis-related proteins, and analogs thereof, that can be labeled isotopically, or with other molecules or proteins, for use in the detection and visualization of angiogenesis-related protein binding sites with techniques, including, but not limited to, positron emission tomography, autoradiography, flow cytometry, radioreceptor binding assays, and immunohistochemistry.

The peptides and analogs of the present invention also act as agonists and antagonists for ANGIOSTATIN™ protein or ENDOSTATIN™ protein receptors, thereby enhancing or blocking the biological activity of ANGIOSTATIN™ protein or ENDOSTATIN™ protein. Such peptides and proteins are used in the isolation of ANGIOSTATIN™ protein or ENDOSTATIN™ protein receptors.

The present invention includes molecular probes for the ribonucleic acid and deoxyribonucleic acid involved in transcription and translation of angiogenesis-related protein binding peptides and proteins. These molecular probes provide means to detect and measure angiogenesis-related protein biosynthesis in tissues and cells.

Accordingly, it is an object of the present invention to provide compositions and methods comprising peptides and proteins that bind angiogenesis-related peptides and proteins.

It is another object of the present invention to provide compositions and methods for treating diseases and processes that are mediated by angiogenesis.

It is yet another object of the present invention to provide diagnostic or prognostic methods and kits for detecting the presence and amount of angiogenesis-related protein binding peptides in a body fluid or tissue.

It is yet another object of the present invention to provide compositions and methods for treating diseases and processes that are mediated by angiogenesis including, but not limited to, hemangioma, solid tumors, blood borne tumors, leukemia, metastasis, telangiectasia, psoriasis, scleroderma, pyogenic granuloma, myocardial angiogenesis, Crohn's disease, plaque neovascularization, coronary collaterals, cerebral collaterals, arteriovenous malformations, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, Helicobacter related diseases, fractures, keloids, vasculogenesis, hematopoiesis, ovulation, menstruation, placentation, and cat scratch fever.

It is another object of the present invention to provide compositions and methods for treating or repressing the growth of a cancer.

Another object of the present invention to provide compositions and methods for the detection or prognosis of cancer.

It is another object of the present invention to provide compositions and methods for use in visualizing and quantitating sites of ANGIOSTATIN™ protein or ENDOSTATIN™ protein binding in vivo and in vitro.

It is yet another object of the present invention to provide compositions and methods for use in detection and quantification of ANGIOSTATIN™ protein or ENDOSTATIN™ protein biosynthesis.

Another object of the present invention to provide receptors that bind angiogenesis-related proteins, such as ANGIOSTATIN™ protein or ENDOSTATIN™ protein.

Yet another object of the present invention is to identify proteins, and fragments thereof, that interact and regulate the activity of angiogenesis-related proteins such as ANGIOSTATIN™ protein or ENDOSTATIN™ protein.

Still another object of the present invention is to provide proteins, and fragments thereof, that are involved in the transport of angiogenesis-related proteins such as ANGIOSTATIN™ protein or ENDOSTATIN™ protein.

Another object of the present invention is to provide proteins, and fragments thereof that function as substrates through which angiogenesis-related proteins exert their activities.

It is yet another object of the present invention to provide a therapy for cancer that has minimal side effects.

Still another object of the present invention is to provide methods and compositions comprising peptides, that bind ANGIOSTATIN™ protein and/or ENDOSTATIN™ protein, linked to a cytotoxic agent for treating or repressing the growth of a cancer.

It is another object of the present invention to provide fusion proteins comprising peptides or proteins' that bind ANGIOSTATIN™ protein and/or ENDOSTATIN™ protein.

Another object of the present invention is to provide methods and compositions for targeted delivery of angiogenesis-related protein compositions to specific locations.

Yet another object of the invention is to provide compositions and methods useful for gene therapy for the modulation of angiogenic processes.

These and other objects, features and advantages of the present invention will become apparent after a review of the following detailed description of the disclosed embodiments and the appended claims.

BRIEF DESCRIPTION OF THE FIGURES

FIG. 2 shows the preferred amino acid sequence of human ANGIOSTATIN™ protein.

FIG. 3 shows the preferred amino acid sequence of human ENDOSTATIN™ protein.

FIG. 4 provides graphs demonstrating binding preference of linear peptides (selected by display technology) for ANGIOSTATIN™ protein over plasminogen.

FIG. 5 provides graphs demonstrating binding preference of cyclized peptides (selected by display technology) for ANGIOSTATIN™ protein over plasminogen.

DETAILED DESCRIPTION

Figure 1:
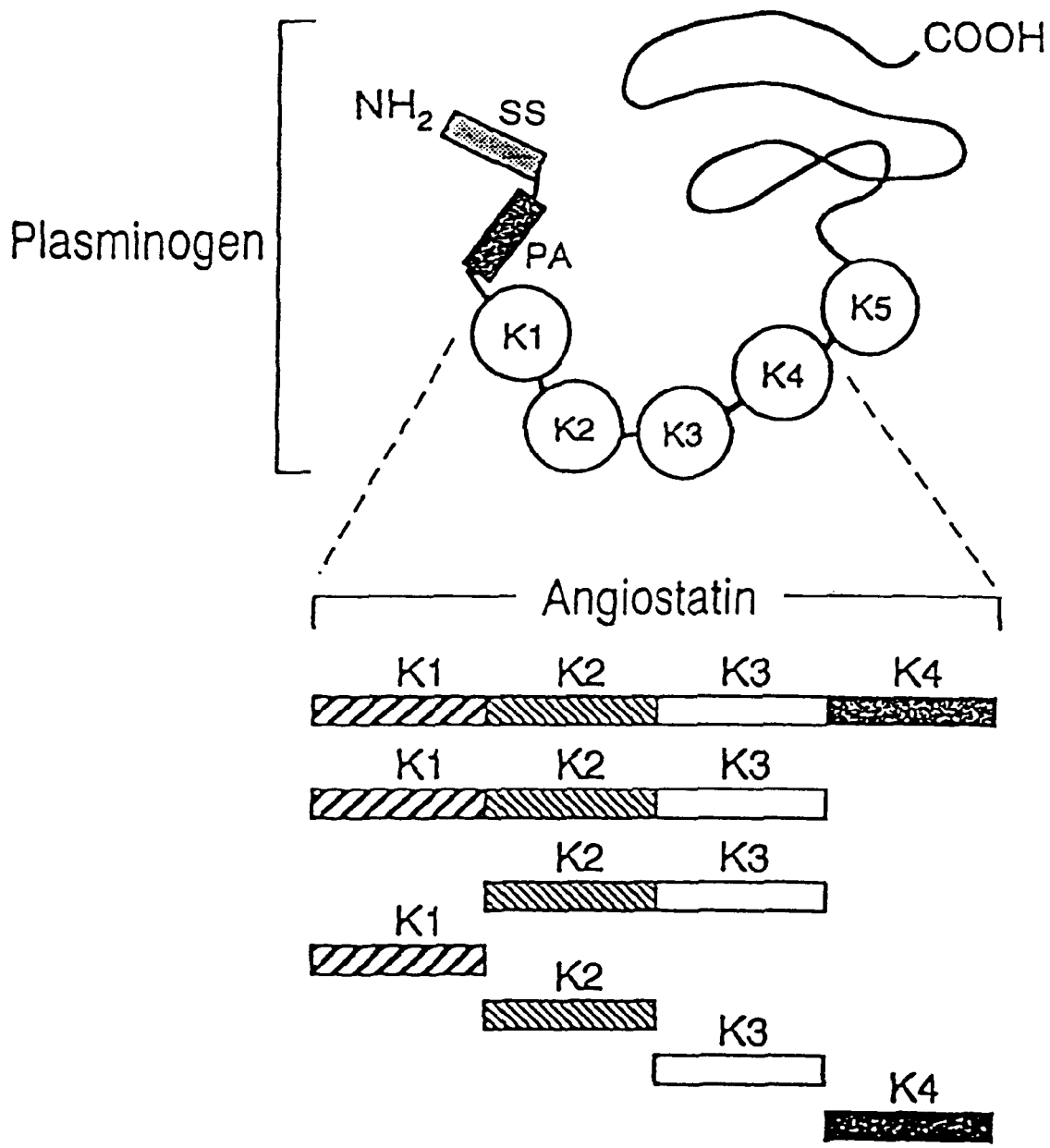
FIG. 1 shows a schematic representation of the structure of human plasminogen and its kringle fragments. Human plasminogen is a single chain protein containing 791 amino acids with one site of N-linked glycosylation at $Asn^{289}$. The non-protease region of human plasminogen consists of the N-terminal 561 amino acids existing in five separate domains, termed kringles as shown in circles (K1, K2, K3, K4 and K5), along with the protein sequences (or with the amino acids) that separate these structures. Each triple disulfide bonded kringle contains approximately 80 amino acids. Angiostatin covers the first 4 of these kringle domains (K1–4), kringle 3 (K1–3) and kringle 4 (K4) are obtained by digestion of human plasminogen with elastase. The rest of the kringle fragments are recombinant proteins expressed in *E. coli*. SS=signal sequence. PA=preactivation protein.

The following description includes the best presently contemplated mode of carrying out the invention. This description is made for the purpose of illustrating the general principles of the inventions and should not be taken in a limiting sense.

As used herein, the term "ANGIOSTATIN™ protein" refers to a protein containing approximately kringle regions 1 through 4 of a plasminogen molecule and having a molecular weight of between approximately 38,000 Daltons and 45,000 Daltons as determined by reducing polyacrylamide gel electrophoresis. ANGIOSTATIN™ protein preferably has an amino acid sequence substantially similar to that of a fragment of murine plasminogen beginning at approximately amino acid number 98. The description of ANGIOSTATIN™ protein as provided in U.S. Pat. No. 5,639,725 to O'Reilly et al. is herein incorporated by reference in its entirety. A preferred amino acid sequence for human ANGIOSTATIN™ protein is shown in FIG. 2.

As used herein, the term "ENDOSTATIN™ protein" refers to a protein that is a collagen molecule fragment and has a molecular weight of between approximately 18,000 Daltons and 20,000 Daltons as determined by non-reducing and reducing electrophoresis, respectively. The preferred sequence of the first N-terminal amino acids of ENDOSTATIN™ protein corresponds to a C-terminal fragment of collagen type XVIII or XV. The description of ENDOSTATIN™ protein as provided in U.S. patent application Ser. No. 08/740,168 and WO 97/15666 O'Reilly et al., is herein incorporated by reference in its entirety. A preferred amino acid sequence for human ENDOSTATIN™ protein is shown in FIG. 3.

As used herein, the term "angiogenesis-related protein" refers to ANGIOSTATIN™ protein and ENDOSTATIN™ protein, and active fragments and homologs thereof, involved in blood vessel growth.

The term "angiogenesis-related protein" includes proteins that are animal or human in origin and also includes proteins that are made synthetically by chemical reaction, or by recombinant technology in conjunction with expression systems.

As used herein, the term "binding peptide" refers to peptides, active fragments and homologs thereof, that bind angiogenesis-related proteins. It will be understood by those skilled in the art that the preferred binding peptides include peptide analogs, which are defined herein as peptides capable of binding angiogenesis-related proteins. Exemplary binding peptides, their amino acid sequences (SEQ ID NOS: 3–28 and SEQ ID NOS: 31–42), and their experimental abbreviations are set forth in the description below. The binding peptides and proteins herein are other than naturally occurring immunoglobulin antibody molecules.

The terms "a", "an" and "the" as used herein are defined to mean "one or more" and include the plural unless the context is inappropriate. As employed herein, the phrase "biological activity" refers to the functionality, reactivity, and specificity of compounds that are derived from biological systems or those compounds that are reactive to them, or other compounds that mimic the functionality, reactivity, and specificity of these compounds. Examples of suitable biologically active compounds include enzymes, antibodies, antigens and proteins.

The term "bodily fluid," as used herein, includes, but is not limited to, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, and vitreal fluid, and nasal secretions.

Unless defined otherwise, all technical and scientific terms used herein have the same meaning as commonly understood by one having ordinary skill in the art to which this invention belongs. Although other materials and methods similar or equivalent to those described herein can be used in the practice or testing of the present invention, the preferred methods and materials are now described.

The present invention includes methods and compositions for the detection and treatment of diseases and processes that are mediated by or associated with angiogenesis. The compositions comprise peptides, proteins, active fragments and homologs thereof, that are capable of binding to angiogenesis-related proteins. In particular, the peptides and proteins are capable of interacting with or binding to ANGIOSTATIN™ protein and/or ENDOSTATIN™ protein.

The present invention includes the use of peptides and proteins such as receptors, that bind angiogenesis-related proteins for detection of angiogenesis-related proteins, such as ANGIOSTATIN™ protein and ENDOSTATIN™ protein, in body fluids and tissues for the purpose of diagnosis or prognosis of diseases such as cancer. In addition, the present invention also includes the detection of ANGIOSTATIN™ protein and ENDOSTATIN™ protein binding sites and receptors in cells and tissues. The present invention further includes methods of treating or preventing angiogenic diseases and processes including, but not limited to, arthritis and tumors by using protein binding peptides for altering the production, administration and activity of ANGIOSTATIN™ protein or ENDOSTATIN™ protein. It is to be understood that the proteins and peptides that bind angiogenesis-related proteins such as ANGIOSTATIN™ protein or ENDOSTATIN™ protein can be animal or human in origin. Such binding peptides can also be produced synthetically by chemical reaction or by recombinant techniques in conjunction with expression systems.

Angiogenesis-related proteins can be isolated from body fluids including, but not limited to, serum, urine and ascites, or synthesized by chemical or biological methods (including cell culture, recombinant gene expression, peptide synthesis). The proteins may also be obtained by in vitro enzymatic catalysis of plasminogen or plasmin to yield active ANGIOSTATIN™ protein, or of collagen to yield active ENDOSTATIN™ protein. Amino acid sequences of preferred peptides and proteins that bind ANGIOSTATIN™ protein or ENDOSTATIN™ protein are provided as SEQ ID NOS: 3–28 and 31–42. Recombinant techniques include gene amplification from DNA sources using the polymerase chain reaction (PCR), and gene amplification from RNA sources using reverse transcriptase/PCR. General references for methods that can be used to perform the various PCR and cloning procedures described herein can be found in Molecular Cloning: A Laboratory Manual (Sambrook et al., eds. Cold Spring Harbor Lab Publ. 1989, latest edition), which is hereby incorporated by reference. Both ANGIOSTATIN™ protein and ENDOSTATIN™ protein inhibit the growth of blood vessels into tissues such as unvascularized or vascularized tumors.

The present invention further encompasses compositions and methods comprising, vectors containing nucleotide sequences encoding peptides and proteins capable of binding angiogenesis-related proteins such as ANGIOSTATIN™ protein or ENDOSTATIN™ protein, wherein the vector is capable of expressing such binding peptides when present in a cell, a composition comprising a cell containing such a vector. Nucleotide sequences of preferred peptides and proteins that bind ANGIOSTATIN™ protein or ENDOSTATIN™ protein are provided as SEQ ID NOS: 43–80. Because of degeneracy in the genetic code, alternative nucleotide sequences can code for a peptide with the same sequence. The present invention further includes a method comprising, implanting into a human or non-human animal, a cell containing such a vector.

The present invention also encompasses gene therapy whereby genes encoding peptides that bind angiogenesis-related proteins, such as ANGIOSTATIN™ protein or ENDOSTATIN™ protein, are regulated in a patient. Various methods of transferring or delivering DNA to cells for expression of the gene product protein, otherwise referred to as gene therapy, are disclosed in Gene Transfer into Mammalian Somatic Cells in vivo, N. Yang, Crit. Rev. Biotechn. 12(4): 335–356 (1992), which is hereby incorporated by reference. Gene therapy encompasses incorporation of DNA sequences into somatic cells or germ line cells for use in either ex vivo or in vivo therapy. Gene therapy functions to replace genes, augment normal or abnormal gene function, and to combat infectious diseases and other pathologies.

Methods for treating medical problems with gene therapy include therapeutic strategies such as identifying the defective gene and then adding a functional gene to either replace the function of the defective gene or to augment a slightly functional gene; or prophylactic strategies, such as adding a gene for the product protein that will treat the condition or that will make the tissue or organ more susceptible to a treatment regimen. As an example of a prophylactic strategy, a gene for a peptide or protein that binds to ANGIOSTATIN™ protein may be placed in a patient to modify the occurrence of angiogenesis.

Many protocols for transfer of peptide DNA or peptide regulatory sequences are envisioned in this invention. Examples of such technology is found in Transkaryotic Therapies, Inc., of Cambridge, Mass., using homologous recombination to insert a "genetic switch" that turns on an erythropoietin gene in cells. See Genetic Engineering News, Apr. 15, 1994. Such "genetic switches" could be used to activate the desired peptide in cells not normally expressing the corresponding gene.

Gene transfer methods for gene therapy fall into three broad categories-physical (e.g., electroporation, direct gene transfer and particle bombardment), chemical (lipid-based carriers, or other non-viral vectors) and biological (virus-derived vector and receptor uptake). Gene therapy methodologies can also be described by delivery site. Fundamental ways to deliver genes are familiar to those skilled in the art and include ex vivo gene transfer, in vivo gene transfer, and in vitro gene transfer.

Chemical methods of gene therapy may involve a lipid based compound (such as lipofectins or cytofectins), not necessarily a liposome, to ferry the DNA across the cell membrane. Another chemical method may use receptor-based endocytosis, which involves binding a specific ligand to a cell surface receptor and enveloping and transporting it across the cell membrane. The ligand binds to the DNA and the whole complex is transported into the cell. The ligand gene complex is injected into the blood stream and then target cells that have the receptor will specifically bind the ligand and transport the ligand-DNA complex into the cell.

Many gene therapy methodologies employ viral vectors to insert genes into cells. For example, altered retrovirus vectors have been used in ex vivo methods to introduce genes into peripheral and tumor-infiltrating lymphocytes, hepatocytes, epidermal cells, myocytes, or other somatic cells. These altered cells are then introduced into the patient to provide the gene product from the inserted DNA.

Viral vectors have also been used to insert genes into cells using in vivo protocols. To direct tissue-specific expression of foreign genes, cis-acting regulatory elements or promoters that are known to be tissue specific can be used. Alternatively, this can be achieved using in situ delivery of DNA or viral vectors to specific anatomical sites in vivo. A viral vector can be delivered directly to the in vivo site, by a catheter for example, thus allowing only certain areas to be infected by the virus, and providing long-term, site specific gene expression. In vivo gene transfer using retrovirus vectors has also been demonstrated in mammary tissue and hepatic tissue by injection of the altered virus into blood vessels leading to the organs.

Fundamental advantages of retroviral vectors for gene transfer include efficient infection and gene expression in most cell types, precise single copy vector integration into target cell chromosomal DNA, and ease of manipulation of the retroviral genome.

According to the methods used herein, a library of phage displaying potential binding peptides was incubated with immobilized angiogenesis-related proteins to select clones encoding recombinant peptides that specifically bound the immobilized angiogenesis-related protein. The phage that encoded the recombinant peptides were amplified after three rounds of biopanning (binding to the immobilized angiogenesis-related proteins) and individual viral plaques, each expressing a different recombinant protein, or binding peptide, were then expanded to produce amounts of peptides sufficient to perform a binding assay.

One possible technique for identifying the angiogenesis-related binding peptides involves the method wherein the DNA encoding recombinant binding peptides can be subsequently modified for ligation into a eukaryotic protein expression vector. This modification entails removal of the 5' secretion signal sequence and the addition of a translation initiation codon that direct translation of the recombinant binding peptide. Stop codons are also incorporated into the construct in a region downstream of the coding sequence. All cloning procedures employed in the development of the present invention were carried out according to standard laboratory practice.

Methods for preparing libraries containing diverse population of various types of molecules such as peptides, polypeptides, protein, and fragments thereof are known in the art and are commercially available (see, for example, Ecker and Crooke, Biotechnology 13:351–360 (1995), and the references cited therein, each of which is incorporated herein by reference).

The phage display libraries used in for present invention include the Ph.D.-7 phage display library (New England BioLabs Cat #8100), a combinatorial library consisting of random peptide 7-mers. The Ph.D.-7 phage display library consists of linear 7-mer peptides fused to the pIII coat protein of M13 via a Gly-Gly-Gly-Ser flexible linker. The library contains $2.8 \times 10^9$ independent clones and is useful for identifying targets requiring binding elements concentrated in a short stretch of amino acids.

Another phage display library used for the present invention includes the Ph.D.-C7C library (New England BioLabs Cat # 8120) which is a combinatorial library consisting of random peptide 7-mers flanked by cysteine residues that under non-denaturing conditions are disulfide bonded resulting in the display of cyclized peptides. In non-reducing conditions, the cysteines form a disulfide bond resulting in each peptide being constrained in a disulfide loop. The library contains $3.7 \times 10^9$ independent clones that like the Ph.D.-7 library the peptides are fused to the pIII coat protein of M13 via a Gly-Gly-Gly-Ser flexible linker. Constrained libraries are useful in the identification of structural epitopes. This library was screened for the binding of 7 amino acid cyclized peptides.

Phage selection was conducted according to methods known in the art and according to manufacturers' recommendations. The "target" proteins, recombinant human ANGIOSTATIN™ protein, or recombinant human ENDOSTATIN™ protein, were coated overnight onto tissue culture plates in humidified containers. In the first round of panning approximately $2 \times 10^{11}$ phage were incubated on the protein coated plate for 60 minutes at room temperature while rocking gently. The plates were then washed several times using standard wash solutions such as TBS (50 mM Tris-HCl (pH 7.5), 150 mM NaCl) containing 0.1% Tween 20. The binding phage were then collected and amplified following elution using the target protein. Secondary and tertiary pannings were performed as necessary.

Following the last screening individual colonies of phage-infected bacteria were picked at random, the phage DNA was isolated and subjected to automated dideoxy sequencing. The sequence of the displayed peptides were deduced from the DNA sequence.

Use of phage-display technology is particularly desirable for the detection of molecules that function as receptors for angiogenesis-related proteins. For example, a specific receptor may be displayed on the surface of the phage such that it may bind its ligand. The receptor can then be modified by, for example, in vitro mutagenesis and variants having higher binding affinity for the ligand selected. As used herein, the term "receptor" means molecule that binds a specific, or group of specific angiogenesis-related proteins. The natural "receptors" could be expressed on the surface of a population of cells, or they could be the extracellular domain of such a molecule (whether such a form exists naturally or not), or a soluble molecule performing natural binding function in the plasma, or within a cell or organ.

Alternatively, the phage-receptor can be used as the basis of a rapid screening system for the binding of ligands such as ANGIOSTATIN™ protein and ENDOSTATIN™ protein, altered ligands, or potential drug candidates. The advantages of this system namely, of simple cloning, convenient expression, standard reagents and easy handling makes the drug screening application particularly attractive.

In addition, the phage-receptor may be used to identify binding peptides and proteins for better understanding, and ultimately modifying, the role of angiogenesis-related proteins in angiogenesis, and in the manifestation of angiogenesis-related disease. For example, the binding peptides may be used to identify proteins that interact with, and/or regulate (either positively or negatively), the activity of angiogenesis-related proteins such as ANGIOSTATIN™ protein or ENDOSTATIN™ protein. In addition, such binding peptides may also be used to identify other proteins and molecules involved in the transport of angiogenesis-related proteins, and substrates through which angiogenesis-related proteins exert their activities.

Following synthesis of the peptides and proteins that bind angiogenesis-related proteins, the peptides and proteins may be added to the in vitro assays to further determine the biological activity of ANGIOSTATIN™ protein or ENDOSTATIN™ protein. These assays are familiar to those skilled in the art and include HUVEC and BCE proliferation assays, HUVEC wound/migration assay, endothelial cell tube forming assay, CAM assay, Matrigel invasion assay and the rat aortic assay. Specifically, the peptides and proteins that inhibit or stimulate the activity of ANGIOSTATIN™ protein or ENDOSTATIN™ protein are identified. The ability of a peptide or protein to inhibit or stimulate the activity of either ANGIOSTATIN™ protein or ENDOSTATIN™ protein in these assays would indicate that the peptide or protein is able to mimic the interaction of ANGIOSTATIN™ protein or ENDOSTATIN™ protein with proteins that regulate their activity.

The biological activity of the binding peptides and proteins may also be tested in vivo. The peptides or proteins may be pre-incubated with their target angiogenesis-related protein (ANGIOSTATIN™ protein or ENDOSTATIN™ protein) prior to being used in either the B16B16 metastasis assay or the Lewis Lung Carcinoma primary tumor or metastasis assays. In such experiments a comparison would be made between the activity of the target protein ANGIOSTATIN™ protein or ENDOSTATIN™ protein and the target protein ANGIOSTATIN™ protein or ENDOSTATIN™ protein pre-bound with the peptide or protein. If the peptide/target protein interactions mimic important biological interactions involved in the activity of ANGIOSTATIN™ protein or ENDOSTATIN™ protein then it would be expected that the anti-angiogenic activity of the target protein would be neutralized by the binding of the peptide or protein.

A complementary approach to determining whether the peptides or proteins mimic the epitopes of proteins that interact with ANGIOSTATIN™ protein or ENDOSTATIN™ protein would be to use the synthesized peptide and protein to generate antibodies. These anti-peptide and anti-protein antibodies would recognize proteins with which ANGIOSTATIN™ protein or ENDOSTATIN™ protein interact. By binding to sites important for the interaction of ANGIOSTATIN™ protein or ENDOSTATIN™ protein with their binding proteins these antibodies would effect the anti-angiogenic activity of the ANGIOSTATIN™ protein or ENDOSTATIN™ protein. Thus, these anti-peptide and anti-protein antibodies can be assayed for their ability to affect the activity of ANGIOSTATIN™ protein or ENDOSTATIN™ protein.

The anti-peptide and anti-protein antibodies may also be used to screen phage expression libraries such as a λgt11 expression library. Such an approach would enable the cloning of the cDNA corresponding to proteins that interact with ANGIOSTATIN™ protein or ENDOSTATIN™ protein. Once the cDNAs have been identified they may be produced using recombinant technology and their anti-angiogenic activities in various assays determined alone and in combination with their target angiogenesis-related protein.

Using the methods described above and further described below in the Examples, the peptides in Tables 1–4 have been identified as linear or cyclized peptides that bind ANGIOSTATIN™ protein or ENDOSTATIN™ protein.

Two phage-display libraries were screened, the first was a linear library that encoded for linear 7 residue peptides, and the second was a disulfide constrained peptide library. Specifically, the second library consisted of 7-mer randomized peptide sequences which were flanked by a pair of cysteine residues. The cysteine residues spontaneously form disulfide cross-links, resulting in the phage displaying cyclized peptides.

TABLE 1

Linear Peptides Binding ANGIOSTATIN ™ Protein

| Peptide | Amino Acid Sequence | SEQ ID NO: |
|---|---|---|
| A1 | E R V N D D T G G G S | SEQ ID NO:3 |
| A3 | D R S G A I K G G G S | SEQ ID NO:4 |
| A7 | L D R A N V F G G G S | SEQ ID NO:5 |
| A9 | S P L G G S E G G G S | SEQ ID NO:6 |
| A10 | H A I Y P R H G G G S | SEQ ID NO:7 |

TABLE 2

Cyclized Peptides Binding ANGIOSTATIN ™ Protein

| Peptide | Amino Acid Sequence | SEQ ID NO: |
|---|---|---|
| A25 | C W S Y E W S K C G G G | SEQ ID NO:8 |
| A31 | C W S L E Q S K C G G G | SEQ ID NO:9 |
| A35 | C W S L E W Q K C G G G | SEQ ID NO:10 |
| A28 | C W S L E T T K C G G G | SEQ ID NO:11 |
| A33 | C W S L E H Q K C G G G | SEQ ID NO:12 |
| A34 | C W S L E I L K C G G G | SEQ ID NO:13 |

TABLE 2-continued

Cyclized Peptides Binding ANGIOSTATIN ™ Protein

| Peptide | Amino Acid Sequence | SEQ ID NO: |
|---|---|---|
| A30 | C W T L E S T K C G G G | SEQ ID NO:14 |
| A32 | C G D M S D R P C G G G | SEQ ID NO:15 |

TABLE 3

Linear Peptides Binding ENDOSTATIN ™ Protein

| Peptide | Amino Acid Sequence | SEQ ID NO: |
|---|---|---|
| E15 | H K R P R N N G G G S | SEQ ID NO:16 |
| E12 | T K H R A G R G G G S | SEQ ID NO:17 |
| E13 | W H R S V W K G G G S | SEQ ID NO:18 |
| E14 | S P Q P F E E G G G S | SEQ ID NO:19 |
| E16 | F T E P T H K G G G S | SEQ ID NO:20 |
| E17 | K D Y A L P P G G D S | SEQ ID NO:21 |
| E18 | S K I A P I M G G G S | SEQ ID NO:22 |
| E20 | W R Q T R K D G G G S | SEQ ID NO:23 |
| E22 | G K P M P P M G G G S | SEQ ID NO:24 |

TABLE 4

Cyclized Peptides Binding ENDOSTATIN ™ Protein

| Peptide | Amino Acid Sequence | SEQ ID NO: |
|---|---|---|
| E37 | C T H W W H K R C G G G S | SEQ ID NO:25 |
| E41 | C S L T P H R Q C G G G S | SEQ ID NO:26 |
| E45 | C E K E K P M T C G G G S | SEQ ID NO:27 |
| E48 | C A P P G L A R C G G G S | SEQ ID NO:28 |

TABLE 5

Linear Peptides that Preferentially Bind to
ANGIOSTATIN ™ protein over Plasminogen

| Peptide | Amino Acid Sequence | SEQ ID NO: |
|---|---|---|
| PAL-49 | K C C Y Y A K G G G S | SEQ ID NO:31 |
| PAL-51 | K C C Y P S A G G G S | SEQ ID NO:32 |
| PAL-54 | R Q P P H L H G R G S | SEQ ID NO:33 |
| PAL-56 | H K Y I S A T G G G S | SEQ ID NO:34 |
| PAL-66 | G T L Q V L S G G G S | SEQ ID NO:35 |
| PAL-69 | K C C Y S V G G G G S | SEQ ID NO:36 |
| PAL-70 | M S Y Q W S H G G G S | SEQ ID NO:37 |

TABLE 6

Cyclized Peptides that Preferentially Bind to
ANGIOSTATIN ™ protein over Plasminogen

| Peptide | Amino Acid Sequence | SEQ ID NO: |
|---|---|---|
| PAC-77 | C W S L E H S K C G G G S | SEQ ID NO:38 |
| PAC-78 | C V H S I E R E C G G G S | SEQ ID NO:39 |
| PAC-82 | C Y T L P P K L C G G G S | SEQ ID NO:40 |
| PAC-88 | C W S Y E W S K C G G G S | SEQ ID NO:41 |
| PAC-91 | C W S L E W Q K C G G G S | SEQ ID NO:42 |

Nucleic acid sequences corresponding to the above amino acid sequences are provided as SEQ ID NOS: 43–80.

The present invention encompasses the peptides set forth in Tables 5 and 6 which preferentially bind to ANGIOSTATIN™ protein as opposed to plasminogen. The preferential binding activity of the peptides illustrate that a preferred ANGIOSTATIN™ protein receptor is one of these peptides.

In addition, the present invention is related to proteins which share homologous sequences to the claimed peptides. Such proteins include human possible global transcription activator, phosphopentomutase, ribonuclease RH precursor, soybean early nodulin, JNK activating kinase 1, IL-12 beta chain, glutathione reductase, soy bean trypsin inhibitor (kunitz), fibroblast growth factor-6, chemotaxis protein, annexin XI, WEE 1, RAS suppressor protein 1, ATP synthase gamma chain, thioredoxin, collagenese, glycoprotein B-1 precursor, dehydroquinate dehydratase, complement component C8 beta, chain, ornithine decarboxylase antizyme, adenylate cyclase, and ATP synthase, alpha chain.

The homology searches for the present invention were conducted using the FASTA sequence similarity search. The peptide sequences were queried against the SwissProt data base using the default setting (ktup 2, and BLOSUM50 for the scoring matrix). The searches were conduced using the world wide web at site http://www.fasta.genome.adjp/. as described by W. R. Pearson & D. J. Lipman PNAS 85:2444–2448 (1988), which is incorporated in its entirety herein by reference.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Identification of Angiogenesis-Related Binding Peptides

A "phage-display library" is a protein expression library, constructed in a vector that expresses a collection of cloned protein sequences as fusions with a phage coat protein. Thus, in the context of the present invention, single-chain recombinant proteins having the potential ability to bind angiogenesis-related proteins, are expressed as fusion proteins on the exterior of the phage particle. This "placement" advantageously allows contact and binding between the recombinant binding protein and an immobilized protein such as ANGIOSTATIN™ protein or ENDOSTATIN™ protein.

Phage that bind an angiogenesis-related protein can be recovered; individual phage can then be cloned and the peptide expressed by cloned phage can be determined. Phage clones expressing binding peptides specific for angiogenesis-related proteins can be substantially enriched by serial rounds of phage binding to the immobilized protein and amplification by growth in bacterial host cells.

Methods for preparing libraries containing diverse population of various types of molecules such as peptides, polypeptides, protein, and fragments thereof are well known in the art and are commercially available (see, for example, Ecker and Crooke, Biotechnology 13:351–360 (1995), and the references cited therein, each of which is incorporated herein by reference).

Where a molecule is a peptide, protein or fragment thereof, the molecule can be produced in vitro directly or can be expressed from a nucleic acid, which is produced in vitro. Methods of synthetic peptide and nucleic acid chemistry are well known to those skilled in the art.

A library of molecules also can be produced, for example, by constructing a cDNA expression library from mRNA collected from a cell, tissue, organ or organism of interest. Methods for producing such libraries are well known in the art (see, for example, Sambrook et al. Molecular Cloning: A laboratory manual (Cold Spring Harbor Laboratory Press 1989, latest edition) which is incorporated herein by reference. Preferably, the peptide encoded by the cDNA is expressed on the surface of a cell or a virus containing the cDNA. For example, cDNA can be cloned into a phage vector wherein, upon expression, the encoded peptide is expressed as a fusion protein on the surface of the phage.

Phage display technology was used to identify peptide and protein sequences that bind ANGIOSTATIN™ protein or ENDOSTATIN™ protein, and also to identify peptides that mimic the effector binding sites of effector molecules that interact with ANGIOSTATIN™ protein and ENDOSTATIN™ protein.

Materials and Methods

Phage Display Libraries

The Ph.D.-7 phage display library (New England BioLabs Cat #8100), a combinatorial library consisting of random peptide 7-mers, was screened for 7 amino acid binding peptides. The Ph.D.-7 phage display library consists of linear 7-mer peptides fused to the pIII coat protein of M13 via a Gly-Gly-Gly-Ser flexible linker. The library contains $2.8 \times 10^9$ independent clones. The Ph.D. library is useful for identifying targets requiring binding elements concentrated in a short stretch of amino acids.

The Ph.D.-C7C library (New England BioLabs Cat # 8120) is a combinatorial library consisting of random peptide 7-mers flanked by cysteine residues that under non-denaturing conditions are disulfide bonded resulting in the display of cyclized peptides. In non-reducing conditions, the cysteines form a disulfide bond resulting in each peptide being constrained in a disulfide loop. The library contains $3.7 \times 10^9$ independent clones that like the Ph.D.-7 library the peptides are fused to the pIII coat protein of M13 via a Gly-Gly-Gly-Ser flexible linker. Constrained libraries are useful in the identification of structural epitopes. The Ph.D.-C7C library was screened for the binding of 7 amino acid cyclized peptides.

This particular library was selected because it contains representatives of all possible 7 mer sequences and is also a well characterized library. In addition, the short target sequences typically bind with few high affinity interactions that allow the identification of strong interactions. In summary, the peptides in this library allow for binding such that peptides bind with greater affinity thereby increasing the likelihood of mimicking the natural ligand of the target protein.

Phage Selection

The phage display libraries were screened following the manufacturers' recommendations. Approximately 100 μg/ml of recombinant human ANGIOSTATIN™ protein, K1–4 protein, or recombinant human ENDOSTATIN™ protein were coated overnight onto 6-mm tissue culture plates at 4° C. in a humidified container. In the first round of panning approximately $2 \times 10^{11}$ phage were incubated on the protein coated plate for 60 minutes at room temperature while rocking gently. The plates were washed 6 times using TBS (50 mM Tris-HCl (pH 7.5), 150 mM NaCl) containing 0.1% Tween 20. The binding phage were collected and amplified following elution using 100 μg/ml of the target protein. Secondary and tertiary pannings were performed as for the primary screen except the TBS washing buffer contained 0.5% Tween 20.

Sequencing of Angiostatin-Related Binding Peptides

Following the tertiary screening, 10–12 individual colonies of phage-infected bacteria were picked at random, the phage DNA was isolated and subjected to automated dideoxy sequencing. The sequence of the displayed peptides were deduced from the DNA sequence.

Results

Peptides presented below in Tables 7–10 were identified as linear or cyclized peptides that bind ANGIOSTATIN™ protein or ENDOSTATIN™ protein.

TABLE 7

Linear Peptides Binding ANGIOSTATIN ™ Protein

| Peptide | Amino Acid Sequence | SEQ ID NO: |
|---|---|---|
| A1 | E R V N D D T G G G S | SEQ ID NO:3 |
| A3 | D R S G A I K G G G S | SEQ ID NO:4 |
| A7 | L D R A N V F G G G S | SEQ ID NO:5 |
| A9 | S P L G G S E G G G S | SEQ ID NO:6 |
| A10 | H A I Y P R H G G G S | SEQ ID NO:7 |

TABLE 8

Cyclized Peptides Binding ANGIOSTATIN ™ Protein

| Peptide | Amino Acid Sequence | SEQ ID NO: |
|---|---|---|
| A25 | C W S Y E W S K C G G G S | SEQ ID NO:8 |
| A31 | C W S L E Q S K C G G G S | SEQ ID NO:9 |
| A35 | C W S L E W Q K C G G G S | SEQ ID NO:10 |
| A28 | C W S L E T T K C G G G S | SEQ ID NO:11 |
| A33 | C W S L E H Q K C G G G S | SEQ ID NO:12 |
| A34 | C W S L E I L K C G G G S | SEQ ID NO:13 |
| A30 | C W T L E S T K C G G G S | SEQ ID NO:14 |
| A32 | C G D M S D R P C G G G S | SEQ ID NO:15 |

TABLE 9

Linear Peptides Binding ENDOSTATIN ™ Protein

| Peptide | Amino Acid Sequence | SEQ ID NO: |
|---|---|---|
| E15 | H K R P R N N G G G S | SEQ ID NO:16 |
| E12 | T K H R A G R G G G S | SEQ ID NO:17 |
| E13 | W H R S V W K G G G S | SEQ ID NO:18 |
| E14 | S P Q P F E E G G G S | SEQ ID NO:19 |
| E16 | F T E P T H K G G G S | SEQ ID NO:20 |
| E17 | K D Y A L P P G G D S | SEQ ID NO:21 |
| E18 | S K I A P I M G G G S | SEQ ID NO:22 |
| E20 | W R Q T R K D G G G S | SEQ ID NO:23 |
| E22 | G K P M P P M G G G S | SEQ ID NO:24 |

TABLE 10

Cyclized Peptides Binding ENDOSTATIN ™ Protein

| Peptide | Amino Acid Sequence | SEQ ID NO: |
|---|---|---|
| E37 | C T H W W H K R C G G G S | SEQ ID NO:25 |
| E41 | C S L T P H R Q C G G G S | SEQ ID NO:26 |
| E45 | C E K E K P M T C G G G S | SEQ ID NO:27 |
| E48 | C A P P G L A R C G G G S | SEQ ID NO:28 |

Example 2

Identification of Binding Peptides that Preferentially Bind ANGIOSTATIN™ protein over Plasminogen Both the linear (Ph.D.-7) and constrained (Ph.D.-C7C) libraries as described in Example 1 were screened for ANGIOSTATIN™ protein specific binding clones: phage that preferentially bind to ANGIOSTATIN™ protein as opposed to plasminogen.

Materials and Methods

Four rounds of screening were performed on both libraries as follows:

Round 1

- $2 \times 10^{11}$ phage bound to ANGIOSTATIN ™ protein coated plate
- plated washed 10 times
- eluted phage with 100 μg/ml plasminogen
- plated washed 10 times
- eluted phage with 100 μg/ml ANGIOSTATIN ™ protein K1-4
- amplified the ANGIOSTATIN ™ protein eluted phage Round 2

- $2 \times 10^{11}$ amplified primary screen ANGIOSTATIN ™ protein eluted phage bound to ANGIOSTATIN ™ protein coated plate
- plated washed 10 times
- eluted phage with 100 μg/ml plasminogen plated washed 10 times eluted phage with 100 μg/ml ANGIOSTATIN ™ protein K1-4
- amplified the ANGIOSTATIN ™ protein eluted phage Round 3

- $2 \times 10^{11}$ amplified secondary screen ANGIOSTATIN ™ protein eluted phage bound to ANGIOSTATIN ™ protein coated plate
- plated washed 10 times
- eluted phage with 200 μg/ml lys-plasminogen
- plated washed 10 times
- eluted phage with 100 μg/ml ANGIOSTATIN ™ protein K1-4
- amplified the ANGIOSTATIN ™ protein eluted phage Round 4

- $2 \times 10^{11}$ amplified tertiary screen ANGIOSTATIN ™ protein eluted phage bound to ANGIOSTATIN ™ protein coated plate
- plated washed 10 times
- eluted phage with 200 μg/ml lys-plasminogen
- plated washed 10 times
- eluted phage with 100 μg/ml ANGIOSTATIN ™ protein K1-4

Eluted phage was titrated and plated at approximately 75 pfu per plate. 24 individual plaques were picked from the linear (clones PAL 49 to PAL-72) and constrained (clones PAC-73 to PAC-96) libraries and the phage amplified.

Untitrated phage were assayed for their ability to bind to ANGIOSTATIN™ protein and plasminogen in an ELISA assay. Four fold dilutions of phage ranging from 1:4 to 1:65 536 were tested. Several phage were identified as have preferential binding to ANGIOSTATIN™ protein as compared to plasminogen. These phage were selected for further analysis.

TABLE 11

Linear Peptides that Preferentially Bind to ANGIOSTATIN ™ protein over Plasminogen

| Peptide | Amino Acid Sequence | SEQ ID NO: |
|---|---|---|
| PAL-49 | K C C Y Y A K G G G S | SEQ ID NO:31 |
| PAL-51 | K C C Y P S A G G G S | SEQ ID NO:32 |
| PAL-54 | R Q P P H L H G R G S | SEQ ID NO:33 |
| PAL-56 | H K Y I S A T G G G S | SEQ ID NO:34 |
| PAL-66 | G T L Q V L S G G G S | SEQ ID NO:35 |

TABLE 11-continued

Linear Peptides that Preferentially Bind to
ANGIOSTATIN ™ protein over Plasminogen

| Peptide | Amino Acid Sequence | SEQ ID NO: |
|---|---|---|
| PAL-69 | K C C Y S V G G G S | SEQ ID NO:36 |
| PAL-70 | M S Y Q W S H G G G S | SEQ ID NO:37 |

TABLE 12

Cyclized Peptides that Preferentially Bind to
ANGIOSTATIN ™ protein over Plasminogen

| Peptide | Amino Acid Sequence | SEQ ID NO: |
|---|---|---|
| PAC-77 | C W S L E H S K C G G G S | SEQ ID NO:38 |
| PAC-78 | C V H S I E R E C G G G S | SEQ ID NO:39 |
| PAC-82 | C Y T L P P K L C G G G S | SEQ ID NO:40 |
| PAC-88 | C W S Y E W S K C G G G S | SEQ ID NO:41 |
| PAC-91 | C W S L E W Q K C G G G S | SEQ ID NO:42 |

Example 3

Comparison of Angiostatin-Related Binding Peptides using Phage Display Technology and ELISA Assays A modified ELISA assay was used to determine specificity of binding of the phage to the target protein as recommended by New England BioLabs. Plates coated with the target proteins (ANGIOSTATIN™ protein, ENDOSTATIN™, plasminogen) were incubated with 4-fold serial dilutions of the phage from approximately $6.25 \times 10^{10}$ to $2 \times 10^5$ phage particles in 96-well plates. The plates were washed 6 times with TBS containing 0.5% Tween 20 followed by incubation with 1:5000 diluted HRP-conjugated anti-M13 antibody (Pharmacia # 27-9411-01). The plates were washed 6 times with TBS containing 0.5% Tween 20 followed by incubation with ABTS ($2,2^3$-AZINO-bis(3-ETHYLBENZ-THIAZOLINE-6 SULFONIC ACID)) Peroxidase substrate solution at room temperature for 10–60 minutes. The plates were read at 410 nm using a Molecular Devices Spectra MAX 250 microplate reader and SOFT-max® Pro software.

As shown in FIGS. 4 and 5, the peptides selected using phage display technology, preferentially bound to target proteins ANGIOSTATIN™ protein over plasminogen.

Example 4

Identification of Proteins Bearing Sequence Homology to Peptides Identified as Binding ANGIOSTATIN™ protein or ENDOSTATIN™ protein A protein database was searched for proteins that share sequence homology with the peptides identified previously as binding ANGIOSTATIN™ protein and ENDOSTATIN™ protein (A1–A11, E12–E22, A25–A36 and E37–E48). Because of the short length of the peptides (the shorter the sequence used in a search the lower the specificity) a significant number of proteins that shared homology with the identified peptides were found. A selection of the peptides with the highest homology or which appear to be biologically interesting are provided in Tables 13 and 14.

The homology searches were conducted using the FASTA sequence similarity search. The peptide sequences were queried against the SwissProt data base using the default setting (ktup 2, and BLOSUM50 for the scoring matrix). The searches were conduced using the world wide web at site http://www.fasta.genome.adjp/. as described by W. R. Pearson & D. J. Lipman PNAS 85:2444–2448 (1988), which is incorporated in its entirety herein by reference.

TABLE 13

Search Results for Homologies Against the
7 amino acid Peptide Sequences

| Protein Containing Homologous Sequence | Source | Level of Homology |
|---|---|---|
| Human possible global transcription activator | Mammalian (Human) | 7 of 7 amino acids with A9 |
| phosphopentomutase | Bacteria | 6 of 7 amino acids plus 1 conserved with A3 |
| ribonuclease RH precursor | Fungi | 6 of 7 amino acids plus 1 conserved with A35 |
| soybean early nodulin | Soybean | 6 of 7 amino acids plus 1 conserved with A25 |
| JNK activating kinase 1 | Mammalian (Human) | 6 of 7 amino acids with A3 |
| IL-12 beta chain | Mammalian (Mouse) | 6 of 7 amino acids with A34 |
| glutathione reductase | Spinach (Chloroplast) | 5 of 7 amino acids plus 2 conserved with A3 |
| Soy bean trypsin inhibitor (kunitz) | Soybean | 5 of 7 plus 1 conserved amino acid with A1 |
| fibroblast growth factor-6 | Human Mouse | 5 of 7 plus 2 conserved amino acid with E18 |
| chemotaxis protein | Bacteria | 5 of 7 plus 1 conserved amino acid with E12 |
| Annexin XI | Human Rabbit Mouse | 5 of 7 plus 1 conserved amino acid with E22 |
| WEE 1 | Yeast | 5 of 7 plus 1 conserved amino acid with A32 |
| RAS suppressor protein 1 | Mammalian (Human) | 5 of 7 A32 |
| ATP synthase gamma chain | Bacteria | 5 of 7 A32 |
| Thioredoxin | Bacteria | 5 of 7 with A1 |

TABLE 14

Search Results for Homologies Against the 7 Amino Acid Peptide
Plus the GGGS Linker Sequence

| Protein Containing Homologous Sequence | Source | Level of Homology |
|---|---|---|
| Collagenese* | Bacteria | 9 of 13 with A32 |
| Glycoprotein B-1 precursor | Virus | 8 of 11 with E12 |
| Dehydroquinate dehydratase | Bacteria | 8 of 11 with E16 |
| Complement component C8 beta chain* | Mammalian (Rat) | 8 of 13 with plus 2 conserved with A25 |
| Ornithine decarboxylase antizyme | Mammalian (Hamster) | 7 of 11 plus 2 conserved with E13 |
| adenylate cyclase | Bacteria | 7 of 11 plus 2 conserved with E20 |
| ATP synthase alpha chain | Bacteria | 6 of 11 plus 4 conserved with A1 |
| ATP synthase alpha chain | Bacteria | 6 of 11 plus 1 conserved with A10 |

*The constrained peptides were 13 amino acids because of the 2 cysteines i.e. C-XXXXXXX-CGGGS.

An additional Selection of peptides having high homology and appearing biologically interesting, are provided in Tables 15 and 16.

TABLE 15

Search Results for Homologies Against the 7 amino acid Peptide Sequences

| Protein Containing Homologous Sequence | Source | Level of Homology |
|---|---|---|
| FLIY PROTEIN PRECURSOR | E. coli bacteria | 6 out of 7 plus 1 conserved with PAL-66 |
| HEMAGGLUTININ-NEURAMINIDASE | Para influenza (Flu Virus) | 6 out of 7 plus 1 conserved with PAL-66 |
| HISTONE H1 | Drosphila (fruit fly) | 6 out of 7 PAL-56 |
| ADP, ATP CARRIER PROTEIN 2 PRECURCOR | Wheat (plant) | 6 out of 7 plus with PAL-66 |
| RIBONUCLEASE 1 PRECURSOR | Thale-cress (plant) | 5 out of 7 plus 2 conserved with PAL-51 |
| CALRETININ | Mouse (mammalian) | 5 out of 7 plus 2 conserved with PAL-53 |
| HYPOTHETICAL 64.1 KD ZINC FINGER PROTEIN | Yeast (eukaryotic) | 5 out of 7 plus 2 conserved with PAL-70 |
| T-CELL SURFACE ANTIGEN CD2 PRECURSOR | Rat and mouse (mammalian) | 5 out of 7 plus 2 conserved with PAL-70 |
| ATP SYNTHASE C CHAIN | Bacillus alcalophilus (bacteria) | 5 out of 7 plus 1 conserved with PAL-66 |
| CELL DIVISION INHIBITOR MINC. | E. coli (bacteria) | 5 out of 7 plus 1 conserved with PAL-56 |
| CELL DIVISION CONTROL PROTEIN 45 | Yeast (eukaryotic) | 5 out of 7 plus 1 conserved with PAC-78 |
| FETAL BRAIN PROTEIN | Human (mammalian) | 5 out of 7 plus 1 conserved with PAL-53 |
| HOLLIDAY JUNCTION DNA HELICASE RUVA | Pseudomonas aeruginosa (bacteria) | 5 out of 7 plus 1 conserved with PAL-53 |

TABLE 16

Search Results for Homologies Against the 7 Amino Acids Plus the GGGS Linker Sequence

| Protein Containing Homologous Sequence | Source | Level of Homology |
|---|---|---|
| CELL WALL PROTEIN QID3 PRECURSOR | Trichoderma harzianum (eukaryotic) | 8 of 13 plus 2 conserved with PAC-82* |
| HYDROPHOBIN PRESURSOR (RODLET PROTEIN) | Aspergillus fumigatus (Eukaryotic) | 8 of 11 plus 1 conserved with PAL-66 |
| CARBOXYPEPTIDASE Y PRECURSOR | Yeast (eukaryotic) | 7 of 13 plus 4 conserved with PAC-78* |
| NODULIN 24 PRECURSOR | Soy Bean (plant) | 7 of 11 plus 2 conserved with PAL-51 |
| HYPOTHETICAL ABC TRANSPORTER PERMEASE PRO | E. coli (bacteria) | 7 of 11 plus 1 conserved with PAL-66 |

*The constrained peptides were 13 amino acids because of the 2 cysteines i.e. C-XXXXXXX-CGGGS.

It should be understood that the foregoing relates only to preferred embodiments of the present invention, and that numerous modifications or alterations may be made therein without departing from the spirit and the scope of the invention as set forth in the appended claims. The references cited throughout are hereby incorporated by reference in their entireties.

We claim:

1. An isolated angiogenesis-inhibiting protein receptor comprising an amino acid sequence selected from the group consisting of SEQ ID NOs:16–28, without the GGGS or GGDS linker.

2. The protein receptor of claim 1, wherein the receptor comprises an amino acid sequence selected from the group consisting of SEQ ID NOs:16–24, without the GGGS or GGDS linker.

3. The protein receptor of claim 1, wherein the receptor comprises a conformational epitope represented by an amino acid sequence selected from the group consisting of SEQ ID NOs:25–28, without the GGGS linker.

4. An isolated endostatin protein binding peptide having a conformational epitope represented by an amino acid sequence selected from the group consisting of SEQ ID NOs:25–28, without the GGGS linker.

5. An isolated endostatin protein binding peptide having an amino acid sequence selected from the group consisting of SEQ ID NOs:16–24, without the GGGS or GGDS linker.

6. An isolated endostatin protein binding peptide having an amino acid sequence selected from the group consisting of SEQ ID NOs:25–28, without the GGGS linker.

* * * * *

SEQUENCE LISTING

```
<160> NUMBER OF SEQ ID NOS: 80

<210> SEQ ID NO 1
<211> LENGTH: 378
<212> TYPE: PRT
<213> ORGANISM: Homo sapiens

<400> SEQUENCE: 1

Leu Phe Glu Lys Lys Val Tyr Leu Ser Glu Cys Lys Thr Gly Asn Gly
  1               5                  10                  15

Lys Asn Tyr Arg Gly Thr Met Ser Lys Thr Lys Asn Gly Ile Thr Cys
             20                  25                  30

Gln Lys Trp Ser Ser Thr Ser Pro His Arg Pro Arg Phe Ser Pro Ala
         35                  40                  45

Thr His Pro Ser Glu Gly Leu Glu Glu Asn Tyr Cys Arg Asn Pro Asp
     50                  55                  60

Asn Asp Pro Gln Gly Pro Trp Cys Tyr Thr Thr Asp Pro Glu Lys Arg
 65                  70                  75                  80

Tyr Asp Tyr Cys Asp Ile Leu Glu Cys Glu Glu Cys Met His Cys
                 85                  90                  95

Ser Gly Glu Asn Tyr Asp Gly Lys Ile Ser Lys Thr Met Ser Gly Leu
                100                 105                 110
```

```
Glu Cys Gln Ala Trp Asp Ser Gln Ser Pro His Ala His Gly Tyr Ile
            115                 120                 125

Pro Ser Lys Phe Pro Asn Lys Asn Leu Lys Lys Asn Tyr Cys Arg Asn
        130                 135                 140

Pro Asp Arg Glu Leu Arg Pro Trp Cys Phe Thr Thr Asp Pro Asn Lys
145                 150                 155                 160

Arg Trp Glu Leu Cys Asp Ile Pro Arg Cys Thr Thr Pro Pro Pro Ser
                165                 170                 175

Ser Gly Pro Thr Tyr Gln Cys Leu Lys Gly Thr Gly Glu Asn Tyr Arg
            180                 185                 190

Gly Asn Val Ala Val Thr Val Ser Gly His Thr Cys Gln His Trp Ser
        195                 200                 205

Ala Gln Thr Pro His Thr His Asn Arg Thr Pro Glu Asn Phe Pro Cys
    210                 215                 220

Lys Asn Leu Asp Glu Asn Tyr Cys Arg Asn Pro Asp Gly Lys Arg Ala
225                 230                 235                 240

Pro Trp Cys His Thr Thr Asn Ser Gln Val Arg Trp Glu Tyr Cys Lys
                245                 250                 255

Ile Pro Ser Cys Asp Ser Ser Pro Val Ser Thr Glu Gln Leu Ala Pro
            260                 265                 270

Thr Ala Pro Pro Glu Leu Thr Pro Val Val Gln Asp Cys Tyr His Gly
        275                 280                 285

Asp Gly Gln Ser Tyr Arg Gly Thr Ser Ser Thr Thr Thr Thr Gly Lys
    290                 295                 300

Lys Cys Gln Ser Trp Ser Ser Met Thr Pro His Arg His Gln Lys Thr
305                 310                 315                 320

Pro Glu Asn Tyr Pro Asn Ala Gly Leu Thr Met Asn Tyr Cys Arg Asn
                325                 330                 335

Pro Asp Ala Asp Lys Gly Pro Trp Cys Phe Thr Thr Asp Pro Ser Val
            340                 345                 350

Arg Trp Glu Tyr Cys Asn Leu Lys Lys Cys Ser Gly Thr Glu Ala Ser
        355                 360                 365

Val Val Ala Pro Pro Val Val Leu Leu
    370                 375

<210> SEQ ID NO 2
<211> LENGTH: 183
<212> TYPE: PRT
<213> ORGANISM: Homo sapiens

<400> SEQUENCE: 2

His Ser His Arg Asp Phe Gln Pro Val Leu His Leu Val Ala Leu Asn
  1               5                  10                  15

Ser Pro Leu Ser Gly Gly Met Arg Gly Ile Arg Gly Ala Asp Phe Gln
             20                  25                  30

Cys Phe Gln Gln Ala Arg Ala Val Gly Leu Ala Gly Thr Phe Arg Ala
         35                  40                  45

Phe Leu Ser Ser Arg Leu Gln Asp Leu Tyr Ser Ile Val Arg Arg Ala
     50                  55                  60

Asp Arg Ala Ala Val Pro Ile Val Asn Leu Lys Asp Glu Leu Leu Phe
 65                  70                  75                  80

Pro Ser Trp Glu Ala Leu Phe Ser Gly Ser Glu Gly Pro Leu Lys Pro
                 85                  90                  95

Gly Ala Arg Ile Phe Ser Phe Asp Gly Lys Asp Val Leu Arg His Pro
```

```
                    100                 105                 110
Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Ser Ser Leu Leu Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser Lys
            180

<210> SEQ ID NO 3
<211> LENGTH: 11
<212> TYPE: PRT
<213> ORGANISM: murine

<400> SEQUENCE: 3

Glu Arg Val Asn Asp Asp Thr Gly Gly Gly Ser
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 4

Asp Arg Ser Gly Ala Ile Lys Gly Gly Gly Ser
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 5

Leu Asp Arg Ala Asn Val Phe Gly Gly Gly Ser
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 6

Ser Pro Leu Gly Gly Ser Glu Gly Gly Gly Ser
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: synthetic
      binding peptides
```

```
<400> SEQUENCE: 7

His Ala Ile Tyr Pro Arg His Gly Gly Gly Ser
  1               5                  10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 8

Cys Trp Ser Tyr Glu Trp Ser Lys Cys Gly Gly Gly Ser
  1               5                  10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 9

Cys Trp Ser Leu Glu Gln Ser Lys Cys Gly Gly Gly Ser
  1               5                  10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 10

Cys Trp Ser Leu Glu Trp Gln Lys Cys Gly Gly Gly Ser
  1               5                  10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 11

Cys Trp Ser Leu Glu Thr Thr Lys Cys Gly Gly Gly Ser
  1               5                  10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 12

Cys Trp Ser Leu Glu His Gln Lys Cys Gly Gly Gly Ser
  1               5                  10

<210> SEQ ID NO 13
<211> LENGTH: 13
<212> TYPE: PRT
```

```
<213> ORGANISM: Artificial Sequence
<220> FEATURE:
<223> OTHER INFORMATION: Description of Artificial Sequence: synthetic
      binding peptides

<400> SEQUENCE: 13

Cys Trp Ser Leu Glu Ile Leu Lys Cys Gly Gly Gly Ser
  1               5                  10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 14

Cys Trp Thr Leu Glu Ser Thr Lys Cys Gly Gly Gly Ser
  1               5                  10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 15

Cys Gly Asp Met Ser Asp Arg Pro Cys Gly Gly Gly Ser
  1               5                  10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 16

His Lys Arg Pro Arg Asn Asn Gly Gly Gly Ser
  1               5                  10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 17

Thr Lys His Arg Ala Gly Arg Gly Gly Gly Ser
  1               5                  10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 18

Trp His Arg Ser Val Trp Lys Gly Gly Gly Ser
  1               5                  10
```

```
<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 19

Ser Pro Gln Pro Phe Glu Glu Gly Gly Gly Ser
  1               5                  10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 20

Phe Thr Glu Pro Thr His Lys Gly Gly Gly Ser
  1               5                  10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 21

Lys Asp Tyr Ala Leu Pro Pro Gly Gly Asp Ser
  1               5                  10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 22

Ser Lys Ile Ala Pro Ile Met Gly Gly Gly Ser
  1               5                  10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 23

Trp Arg Gln Thr Arg Lys Asp Gly Gly Gly Ser
  1               5                  10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: synthetic
      binding peptides
```

<400> SEQUENCE: 24

Gly Lys Pro Met Pro Pro Met Gly Gly Gly Ser
 1               5                   10

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 25

Cys Thr His Trp Trp His Lys Arg Cys Gly Gly Gly Ser
 1               5                   10

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 26

Cys Ser Leu Thr Pro His Arg Gln Cys Gly Gly Gly Ser
 1               5                   10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 27

Cys Glu Lys Glu Lys Pro Met Thr Cys Gly Gly Gly Ser
 1               5                   10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 28

Cys Ala Pro Pro Gly Leu Ala Arg Cys Gly Gly Gly Ser
 1               5                   10

<210> SEQ ID NO 29
<211> LENGTH: 1134
<212> TYPE: DNA
<213> ORGANISM: Homo sapiens

<400> SEQUENCE: 29
ttatttgaaa agaaagtgta tctctcagag tgcaagactg ggaatggaaa gaactacaga      60
gggacgatgt ccaaaacaaa aaatggcatc acctgtcaaa aatggagttc cacttctccc     120
cacagaccta gattctcacc tgctacacac ccctcagagg gactggagga gaactactgc     180
aggaatccag acaacgatcc gcaggggccc tggtgctata ctactgatcc agaaaagaga     240
tatgactact gcgacattct tgagtgtgaa gaggaatgta tgcattgcag tggagaaaac     300

```
tatgacggca aaatttccaa gaccatgtct ggactggaat gccaggcctg ggactctcag      360
agcccacacg ctcatggata cattccttcc aaatttccaa acaagaacct gaagaagaat      420
tactgtcgta accccgatag ggagctgcgg ccttggtgtt tcaccaccga ccccaacaag      480
cgctgggaac tttgcgacat ccccgctgc acaacacctc caccatcttc tggtcccacc       540
taccagtgtc tgaagggaac aggtgaaaac tatcgcggga atgtggctgt taccgtgtcc      600
gggcacacct gtcagcactg gagtgcacag acccctcaca cacataacag gacaccagaa      660
aactttccct gcaaaaattt ggatgaaaac tactgccgca atcctgacgg aaaaagggcc      720
ccatggtgcc atacaaccaa cagccaagtg cggtgggagt actgtaagat accgtcctgt      780
gactcctccc cagtatccac ggaacaattg gctcccacag caccacctga gctaacccct      840
gtggtccagg actgctacca tggtgatgga cagagctacc gaggcacatc ctccaccacc      900
accacaggaa agaagtgtca gtcttggtca tctatgacac cacaccggca ccagaagacc      960
ccagaaaact acccaaatgc tggcctgaca atgaactact gcaggaatcc agatgccgat     1020
aaaggcccct ggtgttttac cacagacccc agcgtcaggt gggagtactg caacctgaaa     1080
aaatgctcag gaacagaagc gagtgttgta gcacctccgc ctgttgtcct gctt           1134

<210> SEQ ID NO 30
<211> LENGTH: 552
<212> TYPE: DNA
<213> ORGANISM: Homo sapiens

<400> SEQUENCE: 30
cacagccacc gcgacttcca gccggtgctc cacctggttg cgctcaacag ccccctgtca       60
ggcggcatgc ggggcatccg cggggccgac ttccagtgct ccagcaggc gcgggccgtg      120 gggctggcgg gcaccttccg cgccttcctg tcctcgcgcc tgcaggacct gtacagcatc      180 gtcgccgtg ccgaccgcgc agccgtgccc atcgtcaacc tcaaggacga gctgctgttt      240
cccagctggg aggctctgtt ctcaggctct gagggtccgc tgaagcccgg ggcacgcatc      300 ttctccttg acggcaagga cgtcctgagg cacccacct ggccccagaa gagcgtgtgg       360
catggctcgg accccaacgg gcgcaggctg accgagagct actgtgagac gtggcggacg      420
gaggctccct cggccacggg ccaggcctcc tcgctgctgg ggggcaggct cctggggcag      480
agtgccgcga gctgccatca cgcctacatc gtgctctgca ttgagaacag cttcatgact      540
gcctccaagt ag                                                         552

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 31

Lys Cys Cys Tyr Tyr Ala Lys Gly Gly Gly Ser
 1               5                  10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: synthetic
      binding peptides
```

-continued

<400> SEQUENCE: 32

Lys Cys Cys Tyr Pro Ser Ala Gly Gly Gly Ser
 1               5                  10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 33

Arg Gln Pro Pro His Leu His Gly Arg Gly Ser
 1               5                  10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 34

His Lys Tyr Ile Ser Ala Thr Gly Gly Gly Ser
 1               5                  10

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 35

Gly Thr Leu Gln Val Leu Ser Gly Gly Gly Ser
 1               5                  10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 36

Lys Cys Cys Tyr Ser Val Gly Gly Gly Gly Ser
 1               5                  10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 37

Met Ser Tyr Gln Trp Ser His Gly Gly Gly Ser
 1               5                  10

<210> SEQ ID NO 38
<211> LENGTH: 13

```
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 38

Cys Trp Ser Leu Glu His Ser Lys Cys Gly Gly Gly Ser
 1               5                  10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 39

Cys Val His Ser Ile Glu Arg Glu Cys Gly Gly Gly Ser
 1               5                  10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 40

Cys Tyr Thr Leu Pro Pro Lys Leu Cys Gly Gly Gly Ser
 1               5                  10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 41

Cys Trp Ser Tyr Glu Trp Ser Lys Cys Gly Gly Gly Ser
 1               5                  10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: synthetic
      binding peptides

<400> SEQUENCE: 42

Cys Trp Ser Leu Glu Trp Gln Lys Cys Gly Gly Gly Ser
 1               5                  10

<210> SEQ ID NO 43
<211> LENGTH: 33
<212> TYPE: DNA
<213> ORGANISM: murine

<400> SEQUENCE: 43
gagcgggtta atgatgattg gggtggaggt tcg                              33

<210> SEQ ID NO 44
```

```
<211> LENGTH: 33
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 44
gatctgtcgg ttgctattaa gggtggaggt tcg                             33

<210> SEQ ID NO 45
<211> LENGTH: 33
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 45
ctggatcggg ctaatgtgtt tggtggaggt tcg                             33

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 46
tcgccgttgg ggggttctga gggtggaggt tcg                             33

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 47
catgctattt atccgcgtca tggtggaggt tcg                             33

<210> SEQ ID NO 48
<211> LENGTH: 36
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 48
tgttggtcgt atgagtggtc gaagtgcggt ggaggt                          36

<210> SEQ ID NO 49
<211> LENGTH: 36
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 49
tgttggagtc tggagcagtc taagtgcggt ggaggt                          36

<210> SEQ ID NO 50
<211> LENGTH: 36
```

<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 50
tgttggtctc ttgagtggca gaagtgcggt ggaggt                               36

<210> SEQ ID NO 51
<211> LENGTH: 36
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 51
tgttggtctc tggagacgac taagtgcggt ggaggt                               36

<210> SEQ ID NO 52
<211> LENGTH: 36
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 52
tgttggtcgc ttgagcatta gaagtgcggt ggaggt                               36

<210> SEQ ID NO 53
<211> LENGTH: 36
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 53
tgttggtctc ntgagattct gaagtgcggt ggaggt                               36

<210> SEQ ID NO 54
<211> LENGTH: 36
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 54
tgttggactt tggagtcgac taagtgcggt ggaggt                               36

<210> SEQ ID NO 55
<211> LENGTH: 36
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 55
tgtggggata tgtctgatcg tccttgcggt ggaggt                               36

<210> SEQ ID NO 56
<211> LENGTH: 33
<212> TYPE: DNA

<213> ORGANISM: Artificial Sequence
<220> FEATURE:
<223> OTHER INFORMATION: Description of Artificial Sequence: synthetic
      binding peptides

<400> SEQUENCE: 56
cataagcgtc ctcgtaataa tggtggaggt tcg                          33

<210> SEQ ID NO 57
<211> LENGTH: 33
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 57
acgaagcatc gtgcggggag gggtggaggt tcg                          33

<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 58
tggcatcggt cggtttggaa gggtggaggt tcg                          33

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 59
agtcctcagc cttttgagga gggtggaggt tcg                          33

<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 60
tttacggagc ctactcataa gggtggaggt tcg                          33

<210> SEQ ID NO 61
<211> LENGTH: 33
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 61
aaggattatg cacttccgcc tggtggagat tcg                          33

<210> SEQ ID NO 62
<211> LENGTH: 33
<212> TYPE: DNA
<213> ORGANISM: Artificial Sequence

```
<220> FEATURE:
<223> OTHER INFORMATION: Description of Artificial Sequence: synthetic
      binding peptides

<400> SEQUENCE: 62
tcgaagattg cgcctattat gggtggaggt tcg                                    33

<210> SEQ ID NO 63
<211> LENGTH: 33
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 63
tggcgtcaga ctaggaagga tggtggaggt tcg                                    33

<210> SEQ ID NO 64
<211> LENGTH: 33
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 64
gggaagccta tgcctccgat gggtggaggt tcg                                    33

<210> SEQ ID NO 65
<211> LENGTH: 36
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 65
tgtacgcatt ggtggcataa gcgttgcggt ggaggt                                 36

<210> SEQ ID NO 66
<211> LENGTH: 36
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 66
tgttctctga cgccgcatcg tcagtgcggt ggaggt                                 36

<210> SEQ ID NO 67
<211> LENGTH: 36
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 67
tgtgagaagg agaagcctat gacgtgcggt ggaggt                                 36

<210> SEQ ID NO 68
<211> LENGTH: 36
<212> TYPE: DNA
<213> ORGANISM: Artificial Sequence
<220> FEATURE:
```

<223> OTHER INFORMATION: Description of Artificial Sequence: synthetic
      binding peptides

<400> SEQUENCE: 68
tgtgcgccgc cgggtctggc gcggtgcggt ggaggt                          36

<210> SEQ ID NO 69
<211> LENGTH: 33
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 69
aagtgttgtt attatgctaa gggtggaggt tcg                             33

<210> SEQ ID NO 70
<211> LENGTH: 33
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 70
aagtgttgtt atccgagtgc gggtggaggt tcg                             33

<210> SEQ ID NO 71
<211> LENGTH: 33
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 71
cgtcagcctc ctcatctgca tggtagaggt tcg                             33

<210> SEQ ID NO 72
<211> LENGTH: 33
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 72
cataagtata tttcggctac tggtggaggt tcg                             33

<210> SEQ ID NO 73
<211> LENGTH: 33
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 73
gggacgttgc aggtgctgtc gggtggaggt tcg                             33

<210> SEQ ID NO 74
<211> LENGTH: 27
<212> TYPE: DNA
<213> ORGANISM: Artificial Sequence
<220> FEATURE:
<223> OTHER INFORMATION: Description of Artificial Sequence: synthetic binding peptides

<400> SEQUENCE: 74
aagtgttgtt attctgtggg gggtgga                                           27

<210> SEQ ID NO 75
<211> LENGTH: 27
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 75
atgtcttatc agtggtcgca tggtgga                                           27

<210> SEQ ID NO 76
<211> LENGTH: 36
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 76
tgttggtctc tggagcattc gaagtgcggt ggaggt                                 36

<210> SEQ ID NO 77
<211> LENGTH: 36
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 77
tgtgttcata gtattgagcg ggagtgcggt ggaggt                                 36

<210> SEQ ID NO 78
<211> LENGTH: 36
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 78
tgttatactt tgcctcctaa gctttgcggt ggaggt                                 36

<210> SEQ ID NO 79
<211> LENGTH: 33
<212> TYPE: DNA
<213> ORGANISM: Artificial Sequence
<220> FEATURE:
<223> OTHER INFORMATION: Description of Artificial Sequence: synthetic
      binding peptides

<400> SEQUENCE: 79
tgttggtcgt atgagtggtc gaagtgcggt gga                                    33

<210> SEQ ID NO 80
<211> LENGTH: 33
<212> TYPE: DNA
<213> ORGANISM: Artificial Sequence
<220> FEATURE:
<223> OTHER INFORMATION: Description of Artificial Sequence: synthetic
      binding peptides

```
<400> SEQUENCE: 80
tgttggtctc ttgagtggca gaagtgcggt gga                    33
```